US012420105B2

(12) United States Patent
Shaker et al.

(10) Patent No.: US 12,420,105 B2
(45) Date of Patent: *Sep. 23, 2025

(54) MEDICAL APPARATUS AND METHOD OF USING THE MEDICAL APPARATUS

(71) Applicant: ALTRIX MEDICAL, INC., Centreville, VA (US)

(72) Inventors: Matthew Robert Shaker, Centreville, VA (US); Daniel Fleck, Potomac, MD (US)

(73) Assignee: Altrix Medical, Inc., Centreville, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/177,755

(22) Filed: Apr. 14, 2025

(65) Prior Publication Data

US 2025/0235709 A1 Jul. 24, 2025

Related U.S. Application Data

(63) Continuation-in-part of application No. 18/827,730, filed on Sep. 7, 2024, now Pat. No. 12,303,703.

(60) Provisional application No. 63/537,084, filed on Sep. 7, 2023.

(51) Int. Cl.
*A61N 1/39* (2006.01)
*A61N 1/04* (2006.01)

(52) U.S. Cl.
CPC ....... *A61N 1/39044* (2017.08); *A61N 1/3925* (2013.01); *A61N 1/3968* (2013.01); *A61N 1/046* (2013.01)

(58) Field of Classification Search
CPC .......................... A61N 1/39044; A61N 1/3925
USPC ............................................... 607/142
See application file for complete search history.

(56) References Cited

U.S. PATENT DOCUMENTS

| | | | |
|---|---|---|---|
| 5,611,815 A | 3/1997 | Cole et al. |
| 5,876,351 A | 3/1999 | Rohde |
| 7,689,278 B2 | 3/2010 | Jonsen |
| 7,715,913 B1 | 5/2010 | Froman et al. |
| 8,335,562 B2 | 12/2012 | Hansen et al. |
| 9,737,701 B2 | 8/2017 | Dupelle et al. |
| 11,331,471 B2 | 5/2022 | Andrews et al. |

(Continued)

FOREIGN PATENT DOCUMENTS

| | | |
|---|---|---|
| WO | 2019070516 A1 | 4/2019 |
| WO | 2021181389 A1 | 9/2021 |

*Primary Examiner* — Nicole F Johnson
(74) *Attorney, Agent, or Firm* — Louis Ventre, Jr.

(57) ABSTRACT

A medical apparatus and a method of using the medical apparatus is disclosed. The method includes a step of providing the medical apparatus configured to perform an initial-state function and further configured to be altered to enable additional medical functions by using adaptor kits containing cartridges and at least one accessory. The initial-state function is one of an updating sequence, a medical diagnostic test, and a medical function. Additional steps include: using the medical apparatus to perform the initial-state function; and altering the medical apparatus to perform two new medical functions. Optional steps include choosing the initial state function, updating the firmware, enabling an ECG using two finger sensors or using multiple leads, providing one or more AED adaptor kits, a wAED adaptor kit, an ECG adaptor kit, and a training AED adaptor kit.

30 Claims, 20 Drawing Sheets

(56) References Cited

U.S. PATENT DOCUMENTS

| | | |
|---|---|---|
| 11,911,627 B1 | 2/2024 | Shaker et al. |
| 2004/0015203 A1 | 1/2004 | McGraw et al. |
| 2009/0171163 A1 | 7/2009 | Mates et al. |
| 2016/0338590 A1* | 11/2016 | Sagalovich ........ A61B 1/00066 |
| 2019/0015657 A1 | 1/2019 | Crutchfield et al. |
| 2020/0282225 A1 | 9/2020 | Kumar et al. |
| 2020/0312453 A1 | 10/2020 | Räisänen et al. |
| 2020/0360707 A1 | 11/2020 | Christiansen et al. |
| 2022/0355122 A1 | 11/2022 | Strommer et al. |

\* cited by examiner

A method of using a medical apparatus, comprising the steps of: 100

Providing Step: providing the medical apparatus configured: to be hand-held by a person; to enable selection of an initial-state function for the medical apparatus; and to accept and operationally integrate into the medical apparatus, an adaptor-kit cartridge from at least one adaptor kit, wherein the contents of each adaptor kit comprise an adaptor-kit cartridge configured to be attached to the medical apparatus, the adaptor-kit cartridge further configured to operationally integrate with the medical apparatus; and each adaptor kit further comprises an accessory, wherein operational integration of the adaptor-kit cartridge and use the accessory are configured to enable a new medical function for the medical apparatus. 105

Using Step: using the medical apparatus to perform the initial-state function. 110

Choosing Step: choosing the initial-state function from the group consisting of: taking an electrocardiogram (ECG) of the person; measuring blood pressure within the person; measuring blood composition within the person; measuring body temperature of the person; measuring a heart rate of the person; measuring acceleration of a chest of the person undergoing cardiopulmonary resuscitation (CPR); coaching in delivery of a medical function; and performing automated electronic defibrillation of the person. 115

Selecting Step: selecting the initial-state function as taking an electrocardiogram (ECG) of the person, identifying a need for an electrocardiogram (ECG) from the person, the person having bare skin accessible to at least two separated sensors, the at least two separated sensors operationally connected to the medical apparatus; and touching the bare skin to the at least two separated sensors operationally connected to the medical apparatus. 120

Configuring Step: configuring the at least two separated sensors to be functional when the person places a finger on each of the separated sensors 125

Supplying Step: supplying the medical apparatus with multiple leads for use in taking the ECG 130

FIG. 1

A method of using a medical apparatus, the method comprising the
steps of:
100

AED-Adaptor Step: providing an AED adaptor kit, the AED adaptor kit
configured to enable the medical apparatus to perform a new medical function
of a reusable non-wearable external defibrillator (AED), the AED adaptor kit
comprises: an AED cartridge and disposable
electrode pads.
205

AED-Connecting Step: connecting the AED cartridge to the medical apparatus
to enable its operation; placing on the person two of the disposable electrode
pads and electrically connecting the disposable-electrode pads to the medical
apparatus either directly or through the AED cartridge.
215

Storing-AED-Pads Step: providing disposable-electrode pads; electrically
connecting the disposable-electrode pads to the medical apparatus and further
configuring the AED adaptor kit to store the disposable-electrode pads while
each such disposable electrode pad is electrically connected to the
AED cartridge.
220 wAED-Adaptor Step: providing a wearable automated external defibrillator
(wAED) adaptor kit, the wAED adaptor kit configured to enable the medical
apparatus to perform a new medical function of a wAED, the wAED adaptor kit
comprising a wAED cartridge configured to connect to, and operationally
integrate with, the medical apparatus; an accessory is also provided.
221 wAED-Harness Step: the wAED adaptor kit further comprises a harness as the
accessory and further comprises the step of securing the harness
on the person.
222 wAED-Implementation Step: connecting the wAED cartridge to the medical
apparatus; and attaching the disposable electrode pads to the person.
223

ECG-Adaptor Step: providing a ECG adaptor kit, the ECG adaptor kit
configured to enable the medical apparatus to perform a third new medical
function of taking an electrocardiogram (ECG), the third adaptor kit comprising:
an ECG cartridge; and a plurality of sensors configured to measure a
magnitude and direction of electrical currents in a heart during each heartbeat.
225

FIG. 2

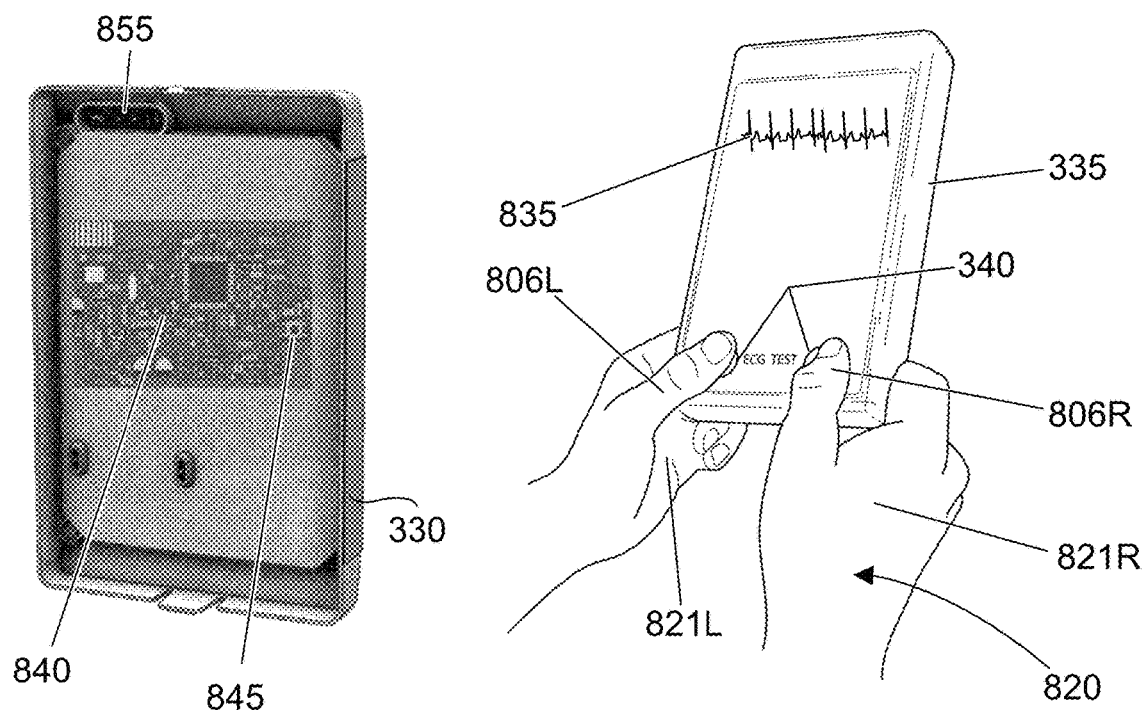
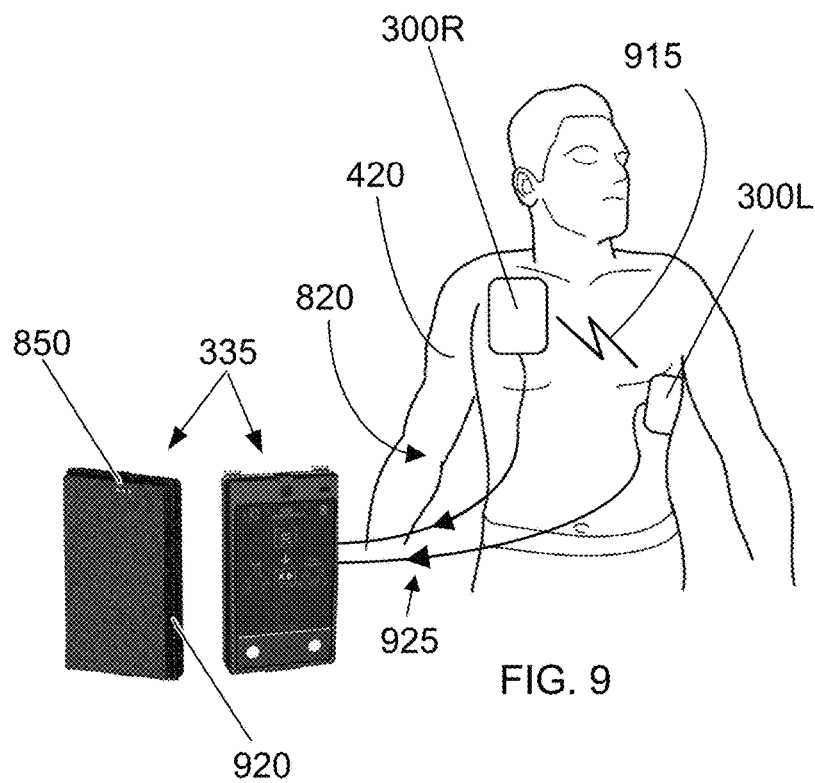
FIG. 8
FIG. 9

| A method of using a medical apparatus, the method comprising the steps of: 100 |
|---|

| AED-Functioning Step: connecting the AED cartridge to the medical apparatus to enable its operation; and placing on the person two of the disposable electrode pads. 1305 |
|---|

| Storing-AED-Pads Step: configuring the AED cartridge to store each of the disposable electrode pads while each such disposable electrode pad is electrically connected to the AED cartridge. 220 |
|---|

| AED Step: enabling the medical apparatus to perform a new medical function of a reusable non-wearable automated external defibrillator. 1306 |
|---|

| AED-Providing Step: The AED-Providing Steps include steps of: providing an AED adaptor kit configured to enable the medical apparatus to perform a new medical function of a reusable non-wearable external defibrillator (AED), the AED adaptor kit comprising: an AED cartridge; and disposable-electrode pads; connecting the AED cartridge to the medical apparatus to enable its operation; and placing on the person two of the disposable-electrode pads. 1310 |
|---|

| wAED-Providing Step: providing a wearable automated external defibrillator (wAED) adaptor kit, the wAED adaptor kit configured to enable the medical apparatus to perform a new medical function of a wAED, the wAED adaptor kit comprising a wAED cartridge configured to connect to, and operationally integrate with, the medical apparatus; an accessory is also provided. 221 |
|---|

| Storing-wAED-Pads Step: providing disposable wAED electrode pads; and further configuring the wAED adaptor kit to store the disposable wAED electrode pads. 1320 |
|---|

| wAED-Harness Step: providing a harness in the wAED adaptor kit; and securing the harness on a person. 222 |
|---|

| wAED-Connecting Step: connecting the wAED cartridge to the medical apparatus; and attaching two disposable electrode pads to the person. 1325 |
|---|

| ECG-Providing Step: providing an ECG adaptor kit, the ECG adaptor kit configured to enable the medical apparatus to perform the new medical function of taking an electrocardiogram (ECG), the ECG adaptor kit comprising: an ECG cartridge; and a plurality of sensors configured to measure a magnitude and direction of electrical currents in a heart during each heartbeat. 1330 |
|---|

FIG. 13

| A method of using a medical apparatus, comprising the steps of: 100 |

| Apparatus-Providing Step: providing a medical apparatus configured to be hand-held and further configured to perform an initial-state function, the initial-state function selected from the group consisting of an updating sequence, and a medical function; and further configured to be transformed to enable performance of at least two different medical functions when modified using at least two adaptor kits that enable different medical functions. 1405 |

| Kit-Providing Step: providing the at least two adaptor kits, each of the adaptor kits, in the at least two adaptor kits, comprises an adaptor-kit cartridge configured to use an accessory, which, when the adaptor-kit cartridge is operationally integrated with the medical apparatus, this operational integration together with the use of the accessory enables operability of the medical apparatus to perform a new medical function. 1406 |

| Accessory-Providing Step: providing the accessory. 1407 |

| Initial-State-Using Step: using the medical apparatus to perform at least one initial-state function. 1408 |

| First-Altering Step: altering the medical apparatus to perform a first new medical function by connecting to the medical apparatus the adaptor-kit cartridge for this first new medical function and by using the accessory for this first new medical function. 1415 |

| First-Removing Step: removing the first adaptor-kit cartridge and stopping use of the first accessory. 1420 |

| Second-Altering Step: altering the medical apparatus to perform a second new medical function by connecting a second adaptor-kit cartridge and by using a second accessory. 1425 |

| Second-Removing Step: removing the second adaptor-kit cartridge and stopping use of the second accessory. 1430 |

| Third-Altering Step: altering the medical apparatus to perform a third new medical function by connecting a third adaptor-kit cartridge and by using a third accessory. 1435 |

FIG. 14

| A method of using a medical apparatus, the method comprising the steps of: 100 |
|---|

| AED-Adaptor Step: providing an AED adaptor kit, the AED adaptor kit configured to enable the medical apparatus to perform a new initial-state function of a reusable non-wearable external defibrillator (AED), the AED adaptor kit comprises: an AED cartridge; and disposable electrode pads. 205 |
|---|

| AED-Connecting Step: connecting the AED cartridge to the medical apparatus to enable its operation; and placing on a person two disposable electrode pads. 215 |
|---|

| Storing-AED-Pads Step: configuring the AED cartridge to store each of the disposable electrode pads while each such disposable electrode pad is electrically connected to the AED cartridge. 220 |
|---|

| Internal-Defibrillation Step: providing an internal-defibrillation adaptor kit, the internal-defibrillation adaptor kit comprising an internal-defibrillation cartridge and internal-defibrillation paddles configured for internal defibrillation; connecting the internal-defibrillation cartridge to the medical apparatus to enable manual defibrillation; connecting the internal-defibrillation paddles to the medical apparatus through the internal-defibrillation cartridge; and placing the internal-defibrillation paddles directly onto a person's heart for defibrillation. 1720 |
|---|

| Pre-Connected Paddles Step: providing an internal-defibrillation adaptor kit, the internal-defibrillation adaptor kit comprising an internal-defibrillation cartridge and internal-defibrillation paddles that are pre-connected to the internal-defibrillation cartridge, the internal-defibrillation paddles configured for internal defibrillation; connecting the internal-defibrillation cartridge to the medical apparatus; and placing the internal-defibrillation paddles directly onto a person's heart for defibrillation. 1725 |
|---|

| Training Step: providing a training AED adaptor kit, the training AED adaptor kit configured to enable the medical apparatus to perform a new initial-state function of training a person to use the medical apparatus as an AED. 1730 |
|---|

FIG. 17

| |
|---|
| A method of using a medical apparatus, the method comprising the steps of: 100 |

| |
|---|
| Hand-Held Step: configuring the medical apparatus to be hand-held so as to be held in a single adult hand while being used. 1905 |

| |
|---|
| Memory-Storage Step: including a memory storage component in each adaptor-kit cartridge in the at least two adaptor kits, the memory storage component configured to store a unique identifier; and further configuring the medical apparatus to enable functionality based on the unique identifier. 1910 |

| |
|---|
| Size-Limiting Step: limiting a weight of the medical apparatus to less than 0.75 kilograms; and further confining a longest dimension of the medical apparatus to a maximum of 16.5 centimeters. 1915 |

| |
|---|
| Initial-State Step: setting the initial-state function of the medical apparatus by connecting to the medical apparatus at least one adaptor-kit cartridge prior to activating the medical apparatus. 1920 |

| |
|---|
| Transmission-Disabling Step: disabling radio transmissions from the medical apparatus by activating a switch for the medical apparatus. 1925 |

| |
|---|
| Function Step: setting two initial-state functions comprising the updating sequence and a pre-programmed self-test, the updating sequence comprising automatically detecting an availability of a firmware update; receiving user initiation to update the firmware; and validating the firmware update using the pre-programmed self-test. 1930 |

| |
|---|
| Processor Step: including a plurality of processors in the medical apparatus; and configuring the plurality of processors to install and validate a firmware upgrade for a medical function, the plurality of processors configured to install and check the integrity of upgraded firmware. 1935 |

FIG. 19

| |
|---|
| A method of using a medical apparatus, the method comprising the steps of:    <u>100</u> |
| AED-Adaptor Step: providing an AED adaptor kit, the AED adaptor kit configured to enable the medical apparatus to perform a new initial-state function of a reusable non-wearable external defibrillator (AED), the AED adaptor kit comprises: an AED cartridge; and disposable electrode pads.    <u>205</u> |
| AED-Connecting Step: connecting the AED cartridge to the medical apparatus to enable its operation; placing on the person two of the disposable electrode pads and electrically connecting the disposable-electrode pads to the medical apparatus either directly or through the AED cartridge..    <u>215</u> |
| Storing-AED-Pads Step: configuring the AED cartridge to store each of the disposable electrode pads while each such disposable electrode pad is electrically connected to the AED cartridge.    <u>220</u> |
| Cartridge Housing Step: comprises the step of framing each adaptor-kit cartridge in a housing configured to connect with the medical apparatus, and wherein at least one of the adaptor-kit cartridges enables a medical function selected from the group consisting of: cardiac defibrillation, cardiac pacing, and electrocardiography.    <u>2005</u> |
| Internal-Adaptor Step: providing an internal-defibrillation adaptor kit, the internal-defibrillation adaptor kit comprising an internal-defibrillation cartridge and internal-defibrillation paddles configured for internal defibrillation; connecting the internal-defibrillation cartridge to the medical apparatus to enable manual defibrillation; connecting the internal-defibrillation paddles to the medical apparatus through the internal-defibrillation cartridge; and placing the internal-defibrillation paddles directly onto a person's heart for defibrillation.    <u>1720</u> |
| Pre-Connected Paddles Step: providing an internal-defibrillation adaptor kit, the internal-defibrillation adaptor kit comprising an internal-defibrillation cartridge and internal-defibrillation paddles that are pre-connected to the internal-defibrillation cartridge, the internal-defibrillation paddles configured for internal defibrillation; connecting the internal-defibrillation cartridge to the medical apparatus; and placing the internal-defibrillation paddles directly onto a person's heart for defibrillation.    <u>1725</u> |
| Training Step: providing a training AED adaptor kit, the training AED adaptor kit configured to enable the medical apparatus to perform a new medical function of training a person to use the medical apparatus as an AED.    <u>1730</u> |

FIG. 20

MEDICAL APPARATUS AND METHOD OF USING THE MEDICAL APPARATUS

CROSS-REFERENCE TO RELATED APPLICATION

This application is a continuation-in-part of U.S. application Ser. No. 18/827,730, filed 7 Sep. 2024, which claimed the benefit of U.S. Provisional Application No. 63/537,084, filed 7 Sep. 2023, which are both hereby incorporated by reference herein in their entirety.

TECHNICAL FIELD

In the field of surgery, a medical apparatus and the method of using the medical apparatus for medical evaluation and treatment of a condition of a living body, the medical apparatus and the method involve the detection of heartbeat electric signals and cardiovascular characteristics. Also, in the field of light, thermal, and electrical application, a device for applying electrical energy to the external surface and inside portions of the body to restore normal operation of the heart.

BACKGROUND ART

An automated external defibrillator (AED), is a medical apparatus designed to be used by a non-medically trained person to help someone who is experiencing a sudden cardiac arrest (SCA). It is designed to deliver an electric charge to the heart in order to restore its normal rhythm. An SCA occurs when the heart's electrical system malfunctions. Such arrythmias cause the heart to stop pumping blood effectively. An AED is designed to detect if a shockable arrythmia is present by using an electrocardiogram (ECG) and, if a shockable arrythmia is present, to provide a therapeutic electric charge. As used herein, the term 'automated external defibrillator' (AED) includes, for the purposes of this specification, (1) devices in which the rescuer determines whether a shock is to be delivered and/or sets the energy level to manually deliver one or more shocks to a patient (i.e., manual defibrillation), (2) devices that assess an arrhythmia and automatically deliver a pre-specified amount of energy one or more times for a patient (automated defibrillation), and (3) devices that assess an arrhythmia and prompt the user to deliver a pre-specified amount of energy one or more times for a patient through interaction with the defibrillator interface (semi-automated defibrillation).

A person who is at high risk of cardiac arrest will sometimes have an implantable cardioverter-defibrillator (ICD) implanted inside their body to be able to perform defibrillation in the event of SCA. While someone at such risk is waiting for that implantation, the person will often be prescribed a wearable AED (wAED) by their physician. The wAED is also known as a wearable cardioverter defibrillator (WCD). The wAED is a special class of AED that can be worn and are typically fully automatic.

Wearable AEDs are prescribed for people who are candidates for an ICD. Such devices are often cumbersome to wear and a patient may discontinue their use because of discomfort. Current technology for a wAED often weighs in excess of 3 pounds. Given the power requirements, a wAED can take up to 16 hours to charge for 12 hours of wear. Both of these factors can be and are improved for wearable AEDs employed using the disclosure herein.

Open chest defibrillation, also known as internal defibrillation, is a procedure in which an electric shock is applied directly to the heart through internal defibrillation paddles. This procedure is typically performed during open-heart surgery when the chest cavity is exposed and the heart is accessible. Internal defibrillation is generally regarded as more effective than external defibrillation because of the direct contact with the myocardium and reduced transthoracic impedance. The need for portable or modular systems capable of delivering internal defibrillation remains unmet in many emergency and field care settings, where traditional defibrillators lack the flexibility or adaptability to support internal paddles. The disclosure herein enables internal defibrillation by means of a dedicated internal-defibrillation adaptor kit, facilitating this advanced function in a portable form factor.

Manual defibrillation is a procedure in which a trained healthcare provider analyzes the patient's cardiac rhythm and determines when and whether to deliver a shock and configured the energy level for the shock. Unlike automated external defibrillators, which assess the heart rhythm and prompt or automate shock delivery based on internal algorithms, manual defibrillation requires real-time clinical decision-making. It is commonly used in hospital and pre-hospital advanced cardiac life support (ACLS) settings. Manual defibrillation may be delivered through disposable electrode pads or through external paddles, and may require synchronized delivery for conditions such as atrial fibrillation. Devices that support both automated and manual defibrillation, while maintaining portability and adaptability, are increasingly valuable in mixed-care environments. The disclosure herein includes the ability to enable manual defibrillation through adaptor kits that allow the user to assume full control of rhythm assessment and shock delivery.

The concept of converting one medical apparatus into a second medical apparatus was first disclosed in patent application Ser. No. 18/343,994 (the '994 patent application), which is hereby incorporated by reference herein. That application disclosed a medical apparatus capable of providing an ECG and also capable of converting to an AED. Disclosed herein is a medical apparatus configured for at least two transformations using adaptor kits. This application effectively describes a hand-held medical apparatus that is physically capable of being converted into at least two additional and separately functioning medical apparatuses.

SUMMARY OF INVENTION

A medical apparatus and a method of using the medical apparatus are disclosed. The method includes a step of providing the medical apparatus configured to perform an initial-state function. The initial-state function is one of an updating sequence, a medical diagnostic test, and a medical function; and further configured to be transformed to enable performance of at least two different medical functions when modified using at least two adaptor kits.

The method further includes a step of providing at least two adaptor kits. Each of the adaptor kits includes an adaptor-kit cartridge and an accessory, which, when the adaptor-kit cartridge and the accessory are operationally integrated with the medical apparatus, this operational integration enables use of the medical apparatus to perform a new medical function.

The method further includes a step of using the medical apparatus to perform the initial-state function.

The method further includes a step of altering the medical apparatus to perform a first new medical function by connecting to the medical apparatus the adaptor-kit cartridge for this first new medical function and by using the accessory in the adaptor-kit cartridge for this first new medical function.

The method further includes a step of removing the adaptor-kit cartridge for the first new medical function and stopping use of an accessory for the first new medical function.

The method further includes a step of altering the medical apparatus to perform a second new medical function by connecting to the medical apparatus the adaptor-kit cartridge for this second new medical function and by using the accessory for this second new medical function.

The method further includes an optional step of removing the adaptor-kit cartridge for this second new medical function and stopping use of the accessory for this second new medical function.

Lastly, the method further includes an optional step of altering the medical apparatus to perform a third new medical function by connecting to the medical apparatus the adaptor-kit cartridge for this third new medical function and by using the accessory for this third new medical function.

BRIEF DESCRIPTION OF DRAWINGS

The drawings illustrate preferred embodiments of a medical apparatus and a method of using a medical apparatus according to the disclosure. The reference numbers in the drawings are used consistently throughout. New reference numbers in FIG. 2 are given the 200 series numbers. Similarly, new reference numbers in each succeeding drawing are given a corresponding series number beginning with the figure number. Dashed lines used in the drawings indicate optional steps or components and solid lines indicate mandatory steps or components.

FIG. 1 is a chart showing two required steps and five optional steps in the method of using the medical apparatus.

FIG. 2 is a continuation of the chart in FIG. 1 showing seven additional optional steps in the method of using the medical apparatus.

FIG. 8 illustrates use of the medical apparatus with two sensors for a person's thumbs.

FIG. 9 illustrates use of the medical apparatus as an AED.

FIG. 13 is a chart of optional steps for the method of providing a medical apparatus.

FIG. 14 is a chart of steps for the method of using the medical apparatus.

FIG. 17 is a chart of optional steps for the method of using the medical apparatus.

FIG. 19 is a chart of optional steps for the method of using the medical apparatus.

FIG. 20 is a chart of optional steps for the method of using the medical apparatus.

DESCRIPTION OF EMBODIMENTS

Figure 3:
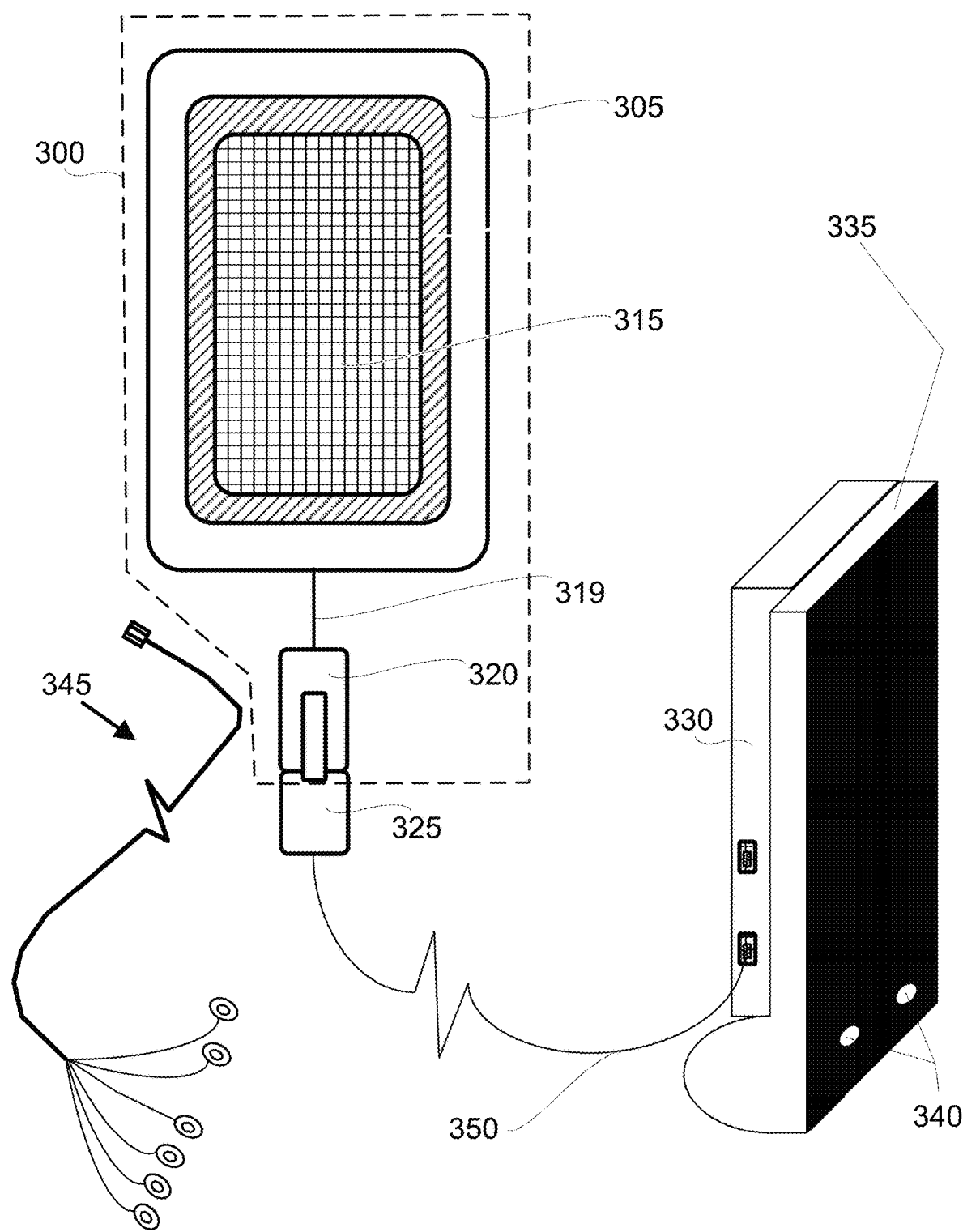
FIG. 3 is a bottom view of a disposable electrode pad, an ECG lead with multiple leads at one end, and a side perspective view of the medical apparatus and an adaptor-kit cartridge connected together.

A method (100) and a medical apparatus (335). The method (100) includes steps for using the medical apparatus (335) that is configured to be physically altered and converted to perform an added or different medical functions. The method (100) may provide for a medical apparatus (335) alterable to a wAED. An initial-state function is any function of the medical apparatus (335) that may be available and chosen at the moment the medical apparatus (335) becomes active and operational, whether due to user interaction (such as pressing a button) or an automatic event (such as the device waking from a lower power mode).

An initial-medical function is a type of initial-state function that is also a medical function. A medical function refers to any diagnostic, monitoring, treatment, or training capability of the medical apparatus (335), whether performed natively or enabled, expanded, or enhanced through an adaptor kit. Medical functions include, but are not limited to, electrocardiography, blood pressure monitoring, automated or manual defibrillation, wearable defibrillation, cardiac pacing, or coaching (1130) in real-time as the CPR is being performed. A medical function may be performed directly by the apparatus, through user interaction, autonomously, or via wired, wireless, or software-based integration with external components.

The medical apparatus (335) preferably starts out with an initial-state function, which is distinguished from the initial-medical function because the initial-state function may be a medical function or more or less than a medical function (for example, it may be a status (1144) of the medical apparatus (335), a self-test (1143), which may be pre-programmed, or AED training and other instructional or simulation-based training on the apparatus, or it may provide coaching (1130) in real-time as the CPR is being performed. Initial-state functions may be initial-medical functions, which are medical functions performed when the device is active. Initial-state functions may also be functions required to ensure that medical apparatus (335) is ready and able to execute one or more medical functions, or functions that support medical functions after those functions are complete (a function ready to be triggered to upload ECG data to the cloud upon completion of an ECG). An initial-state function may be a medical function or support one or more medical functions. An initial-state function becomes available and may be chosen, whether due to user interaction (such as pressing a button or upon the device waking from a lower power mode) or an automatic event. Initial state functions may include: providing a battery status (1145); providing a status (1144) on disposable-electrode pads, which may include status (1144) on disposable-electrode pads (300) designed for use with multiple leads (345) to take an ECG (1148) and may also include status (1144) on disposable-electrode pads (300) designed for defibrillator use that also uses an ECG (835); performing at least one pre-programmed self-test of the medical apparatus (335); firmware (1147) availability notification; firmware upgrade, also referred to herein as Update (1141); providing an error or warning about the medical apparatus (335), or any initial-medical function. An initial-state function may be performed whenever the device is active.

FIGS. 1, 2, 13-15, 17, and 19-21 illustrate steps in the method (100) of using the medical apparatus (335). Required steps in these figures may be connected by a solid line, and the preferred optional steps are connected by dashed lines. The steps may be performed in any sequence or order that complies with the express requirement of a step and that accomplishes the medical function of the method for which the step is performed. Similarly, the steps that are within any given step may also be performed in any sequence or order that complies with the express requirement of that step.

The method (100) of using the medical apparatus (335) may include an Using Step (110); Providing Step (105); an Apparatus-Providing Step (1405); a Second-Apparatus-Providing Step (2105); a Kit-Providing Step (1406); an Accessory-Providing Step (1407); a Second Kit-Providing Step (2106); a Housing Step (2112); a Cartridge Housing Step (2005); a First-Altering Step (1415); a First-Removing Step (1420); a Second-Altering Step (1425).

Other steps for the method (100) may include: a Choosing Step (115); a Selecting Step (120); a Configuring Step (125); a Supplying Step (130); an AED Step (1306); an AED-Adaptor Step (205); an AED-Connecting Step (215); a Storing-AED-Pads Step (220); a wAED-Adaptor Step (221); a wAED-Harness Step (222); a wAED Implementation Step (223); an ECG Adaptor Step (225); an AED-Functioning Step (1305); an AED-Providing Step (1310); a wAED-Adaptor Step (221); a Storing-wAED-Pads Step (1320); a wAED-Harness Step (222); a wAED-Connecting Step (1325); an ECG-Providing Step (1330); a Second-Removing Step (1430); a Third-Altering Step (1435); a Hand-Held Step (1905); a Memory-Storage Step (1910); a Size-Limiting Step (1915); an Initial-State Step (1920); and a Transmission-Disabling Step (1925); a Function Step (1930); a Performance Step (1505); an Updating Step (1510); an ECG Selecting Step (1515); a Configuring Step (125); a Multiple Leads Step (1525); an Internal-Defibrillation Step (1720); a Pre-Connected Paddles Step (1725); and a Training Step (1730).

The Providing Step (105) includes providing a medical apparatus (335) that is configured to be hand-held by a person (420); to enable an initial-state function of the medical apparatus (335); and to accept and operationally integrate any one of multiple adaptor-kit cartridges in adaptor kits; and to use at least one accessory provided from each adaptor kit (1020). Each adaptor kit (1020) comprises at least one of an adaptor-kit cartridge (330), which is configured to physically and/or electronically connect with the medical apparatus (335), may include an accessory (1015) or accessories to be used in conjunction therewith. The accessory (1015) or accessories may also be included outside of the adaptor kit (1020). The adaptor-kit cartridge (330) and the accessory (1015) or accessories are collectively or individually configured to enable, enhance, or expand a medical function of the medical apparatus (335). Whether the accessory (1015) or accessories is included inside or outside the adaptor kit (1020), at least one accessory is required to be used with the adaptor-kit cartridge (330) that is provided in the adaptor kit (1020) to enable, enhance, or expand the medical function. As used herein, "providing" an adaptor kit (1020) or medical apparatus (335) includes any act of making the adaptor kit (1020) available for use in connection with the medical apparatus (335), including but not limited to: manufacturing, assembling, integrating, packaging, shipping, or configuring the item for use, regardless of physical source or commercial channel. "Providing" may also include logical or intended inclusion, even where individual components are supplied separately or at different times.

An accessory (1015) is any physical component, material, or item that enables or supports the intended medical function of the adaptor kit (1020). The accessory (1015) may include, but is not limited to, disposable-electrode pads (300) for external defibrillation (manual and automatic) as well as disposable-electrode pads (300) in a configuration for attachment to multiple leads (345), diagnostic disposables for diagnostic adaptor kits, internal-defibrillation paddles (1800) for open-chest defibrillation, and wearable components such as a harness (405) or belt clips. As used herein, an 'accessory' refers to a physical component that is necessary for, or directly enables, the performance of the medical function associated with an adaptor-kit cartridge (330). In certain embodiments, the adaptor-kit cartridge (330) may include a battery configured to supply power to the medical apparatus (335) itself. In such cases, the battery is considered an accessory (1015) as it enables or supports the medical function of the adaptor kit (1020). This is distinct from batteries that supply power solely to the adaptor-kit cartridge (330), which are not classified as accessories. Instructional or non-functional components are excluded. As used herein, the terms "electrode pad," "disposable-electrode pad," and "patch" are used interchangeably unless the context expressly indicates otherwise. These terms refer to adhesive-backed conductive pads configured for external electrical sensing or therapy. Unless otherwise noted (e.g., training pads), such pads are preferably single-use and disposable.

Figure 10:
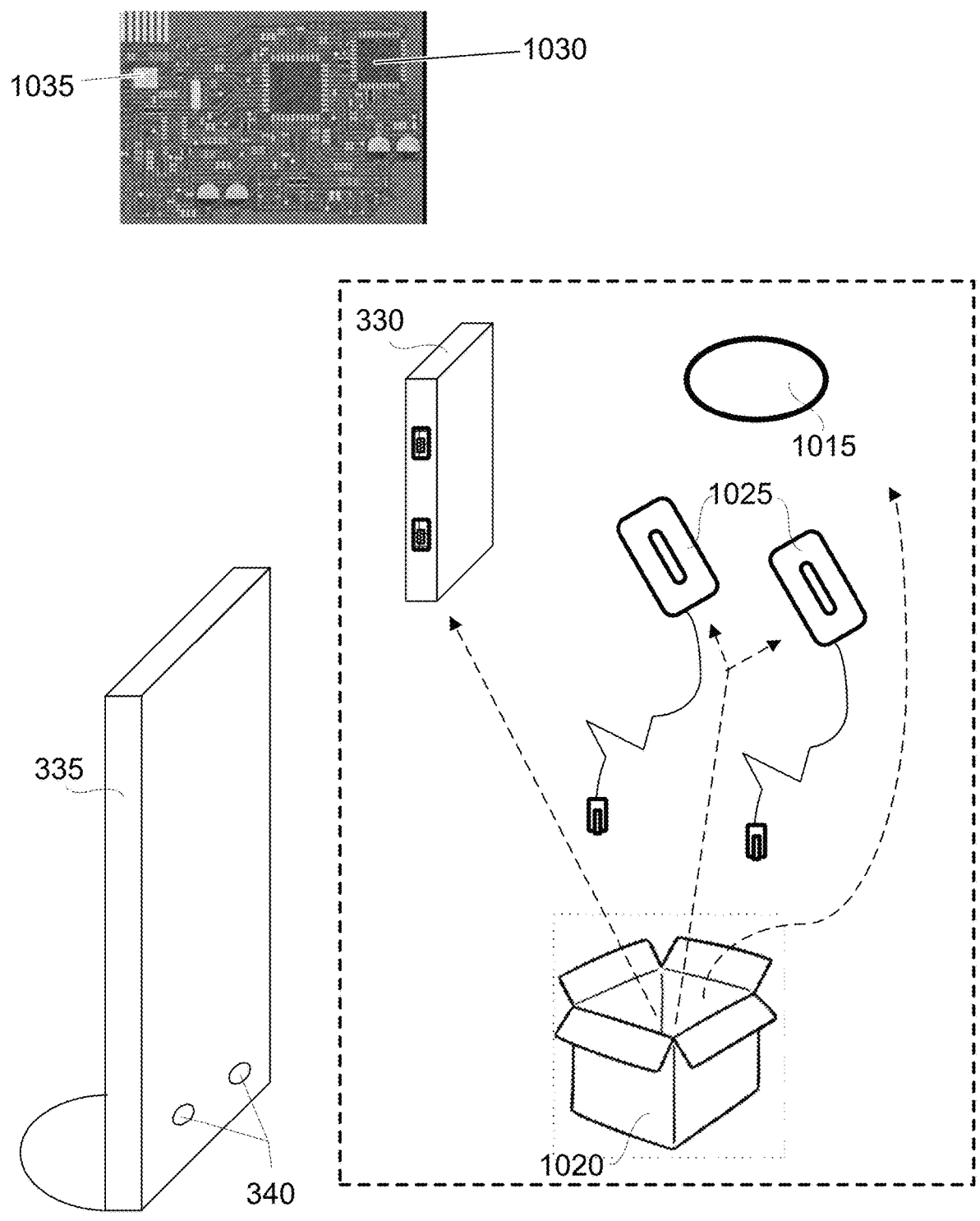
FIG. 10 illustrates internal components of the medical apparatus and within the dashed box the contents or components of a generic adaptor kit to include an adaptor-kit cartridge and an accessory, and also shown is the medical apparatus without any operationally integrated cartridge.

Each adaptor kit (1020) is figuratively shown in FIG. 10 as contents within a dashed box. The contents of each adaptor kit (1020) include an adaptor-kit cartridge (330) and may further include an accessory (1015) or accessories. The accessory (1015) may be provided apart from the adaptor kit (1020).

Each adaptor-kit cartridge (330) in the adaptor kit (1020) is configured to physically and/or electronically attach to and interface with the medical apparatus (335). Each adaptor-kit cartridge (330) is further configured to operationally integrate with the medical apparatus (335) either alone, or in addition to, or instead of another adaptor-kit cartridge (330); and each adaptor kit (1020) may further comprise an accessory (1015) or accessories to be used in aid of delivering the new medical function provided by the adaptor kit (1020). In the method (100), the adaptor-kit cartridge (330) and the accessory (1015) or accessories collectively or individually enable, enhance or expand the medical functionality of the medical apparatus (335). Whether the accessory (1015) or accessories is included inside or outside the adaptor kit (1020), at least one accessory is required to be used with the adaptor-kit cartridge (330) that is provided in the adaptor kit (1020) to enable, enhance, or expand the medical function.

As used herein, the term "adaptor-kit cartridge" refers to a functional module that physically and/or electronically integrates with the medical apparatus (335) and, enables use of an accessory that may accompany the adaptor-kit cartridge (330) in the adaptor kit (1020), and enables a new medical function. The adaptor-kit cartridge (330) may or may not resemble a traditional cartridge in shape or appearance, and may take the form of any housing, plug, interface component, or embedded module that performs this role.

An adaptor-kit cartridge (330) is a unit specifically designed to adapt the medical apparatus (335) to enable, enhance, expand or provide a medical function. The adaptor-kit cartridge (330) and one or more of each of the accessories are necessary to serve the added or different medical function for that adaptor kit (1020). Each accessory (1015) may be an item included with the adaptor-kit cartridge (330) or may be integrated into the adaptor-kit cartridge (330) so as to enable the new medical function, or may be provided separately from the adaptor kit (1020).

The medical apparatus (335) also preferably contains one or more computer processors to run computer code. Different computer code may be run for the medical apparatus (335) without an adaptor-kit cartridge (330) and run for the adaptor-kit cartridge (330) and the accessory (1015).

For the method (100), the Providing Step (105) includes providing the medical apparatus (335) configured with a hand-held (425) to be held by a person (420) while being used to perform an initial-state function or any medical function of the medical apparatus (335). As used herein, "hand-held" refers to a medical apparatus (335) that is dimensioned and configured to be held substantially in a single adult hand (430) while performing at least one initial-state function or at least one medical function.

The medical apparatus (335) may require a second hand for interaction (such as pressing a button), and may rest on a surface or be worn during certain medical functions such as defibrillation or monitoring. However, during performance of at least one initial-state function—such as checking device status—the apparatus can be comfortably supported by one hand. Preferably, the medical apparatus (335) weighs less than 0.75 kilograms and is no more than 16.5 centimeters in its longest dimension.

For example, a hand-held medical apparatus is shown in FIG. 8 for a left hand (821L) or a right hand (821R). An initial-medical function may be enabled by the connection of an initial-state cartridge. Preferably, selection of the initial-medical function is automatic when it is enabled by the addition of the initial-state cartridge that is a training adaptor-kit cartridge (1630). The initial-state cartridge preferably includes electronics to uniquely identify the initial-state cartridge and to automatically relay to the medical apparatus (335) the kind of initial-state cartridge and function it enables. An initial-state cartridge may be an adaptor-kit cartridge (330) that is connected to the medical apparatus (335) before the medical apparatus (335) is activated or powered on. When used with an accessory (1015), the initial-state cartridge that is an adaptor-kit cartridge (330) enables a medical function in the same manner as any adaptor-kit cartridge (330), but is used to configure the medical apparatus (335) in its initial state.

Alternatively, an initial-state cartridge may be used to enable a non-medical function, such as when the training adaptor-kit cartridge (1630) is connected to facilitate AED training. For clarity, initial-state cartridges may be considered a super-set of adaptor-kit cartridges; when an initial-state cartridge is an adaptor-kit cartridge (330), it is counted among the plurality of different medical functions. Accordingly, an adaptor-kit cartridge (330) connected before activation of the medical apparatus (335) qualifies as an initial-state cartridge. An example of an initial-state cartridge that is not an adaptor-kit cartridge (330) is a training adaptor included in a training adaptor kit (1610).

When an adaptor-kit cartridge (330) or training adaptor-kit cartridge (1620) is provided for functioning with the medical apparatus (335), each adaptor-kit cartridge (330) is preferably a "smart cartridge," which includes an identification chip (ID chip) to verify its authenticity and functionality in concert with the medical apparatus (335). The ID chip may include data accessible by the medical apparatus (335). Such data preferably includes a manufacturing date; an installed date; a used date, and compatibility and functionality with the medical apparatus (335). The adaptor-kit cartridge (330) may be configured with a solid-state component to identify certain features or with a unique identification. For example, a resistor of 100 ohms could mean an AED cartridge (630), and 500 ohms could mean wAED cartridge (730), and 10 K ohms could mean an ECG adaptor-kit cartridge (1205).

In addition, it is preferable that any adaptor-kit cartridge (330) storing disposable-electrode pads (300) contains a computer chip that provides a globally unique serial number to enable the medical apparatus (335) to confirm the compatibility of the disposable electrode pad with the cartridge and to enable the medical apparatus (335) to prevent use of an inferior, defective or counterfeit disposable electrode pad and/or cartridge.

In its initial state, the medical apparatus (335) may have an initial-state cartridge attached, or may be configured without the initial-state cartridge. The medical apparatus (335) may be configured for performing one or more medical functions or for performing a self-test, or otherwise providing a status of the medical apparatus (335), providing one or more statuses to the user. If contents of an adaptor kit (1020) are an adaptor-kit cartridge and added to the medical apparatus (335) before an initial-state, such as before it is active or powered up, then up on activation, the first new medical function may be both the initial state function and the initial-medical function provided the accessory (1015) is available.

In one embodiment, the one or more functions in the initial state is at least to take an ECG (835) of the person (420). Preferably, there is an option to sequentially perform all of the diagnostic medical functions in a sequential fashion.

A basic initial-state function is, preferably, to provide a status of the device (e.g., is the medical apparatus (335) ready to and capable of performing possible functions for which it is configured). For example, displaying a battery status.

When the initial-medical function of the medical apparatus (335) is to take an ECG (835), then the medical apparatus (335) may be used repetitively for taking ECGs on one or more persons and its hand-held configuration makes it relatively easy to use for taking multiple ECGs on one person or on multiple persons.

The one or more medical functions in the initial state of the medical apparatus (335) may be a selectable medical function. For example, the medical apparatus (335) may be configured for measuring blood pressure (1105) within the person (420); measuring blood composition (1110) within the person (420); measuring body temperature (1115) of the person (420); measuring a heart rate (1120) of the person (420); measuring chest acceleration (1125) of the person (420) undergoing cardiopulmonary resuscitation (CPR); coaching (1130); performing automated external defibrillation of the person (420) using the disposable-electrode pads for an external defibrillator, e.g., an AED (1135); and performing a diagnostic test. The medical apparatus (335) may default to a medical function in the initial state. Medical functions in the initial state may be enabled by an adaptor kit cartridge and an accessory (1015) or may be native to the medical apparatus (335).

The medical apparatus (335) may be configured to: update (1141) the firmware or software of the medical device; to perform a self-test (1143), which may be pre-programmed, of the medical apparatus (335); and to provide status (1144) information about the medical apparatus (335). A user interface to perform or interact with initial-state functions may be native to the medical apparatus (335), or may be available through a different device, such as a smartphone or tablet. These configurations may occur with or without an adaptor kit (1020), a training adaptor kit (1610), or an accessory (1015).

All of the selectable diagnostic medical functions may be elected by the selection of the "ALL" function (1142). When "ALL" is selected, the medical apparatus (335) performs all of the initial-medical functions that are diagnostic and available to the medical apparatus (335), preferably in a pre-selected logical or sequential order. The user interface to perform or interact with initial-medical functions of the medical apparatus (335) may be native to the medical apparatus (335) or the medical apparatus (335) may be configured to make this function available through a different device, such as a smartphone or tablet. A subset of available medical functions may be selectable on the medical apparatus (335). Certain non-diagnostic initial-state functions may be performed by the medical apparatus (335) without user interaction, such as providing a device status, checking for software or firmware updates or performing an automated self-test.

As used herein, the "ALL" function (1142) refers to a user-selectable or automated command executed by the medical apparatus (335) to sequentially perform all diagnostic medical functions currently available to the device based on its configuration, cartridge integration, and system state. The sequence of diagnostic functions is governed by internal firmware logic or a software-defined order, which may be modified by user settings or system updates. If a function is unavailable due to absence of the required cartridge or accessory (1015), it is skipped. This ensures the "ALL" function adapts dynamically to the capabilities present at the time of execution.

The medical apparatus (335) in the Providing Step (105) is further configured to accept and operationally integrate into the medical apparatus (335) contents (i.e. components) from the adaptor kit (1020), preferably configured to accept and operationally integrate the contents of one or more of a plurality of adaptor kits enabling different medical functions of the medical apparatus (335).

A first content or component of each adaptor kit (1020) comprises an adaptor-kit cartridge (330) configured to be attached to the medical apparatus (335). The attachment of the adaptor-kit cartridge (330) to the medical apparatus (335) operationally integrates the adaptor-kit cartridge (330) into the medical apparatus (335) and together with the accessory (1015) or accessories enables the new medical function.

Each adaptor kit (1020) in the Providing Step (105) may further comprise an accessory (1015) or one or more components needed to perform the added or different medical function. The adaptor-kit cartridge (330) and at least one accessory are required to perform the added or different medical function. Thus, the adaptor-kit cartridge (330) and the accessory (1015) or accessories are configured to support the added or different medical function for the medical apparatus (335). The accessory (1015) may be added to the adaptor-kit cartridge (330) so that it is provided as a single package. An accessory (1015) or accessories may be provided separately, for example, as consumables, and so may be provided as a supplement to the adaptor kit (1020). For purposes of this disclosure, an accessory (1015) is part of the adaptor kit (1020) even if it is physically provided, packaged, or shipped separately, provided that it is intended for use with that adaptor kit (1020) to enable a medical function.

The Initial-State Using Step (1408) is using the medical apparatus (335) to perform an initial-state function. An initial-state function may be one that is fixed or built-in as the initial-state function or enabled by an adaptor kit (1020). The initial-state function may be selected by a user when operating the medical apparatus (335), or may be an automated function provided by the medical apparatus (335). The initial-state function may be preprogrammed in medical apparatus (335), which may have multi-function capabilities.

One such medical function capability that may be an initial-medical function is taking measurements of sound and/or bio-electrical signals from the bare skin (820) of the person (420) using the at least two separated sensors (340) when placed on the bare skin (820) of the person (420).

The at least two separated sensors (340) may be configured to detect a low electric current between them on the bare skin (820). Sensors for making these measurements are well known and are possible by detecting the body's electrical signals emanating from the person, allowing for single-lead ECGs.

In the method (100), the Housing Step (2112) may be included and may include a step of installing the contents of each adaptor-kit cartridge (330) in a housing (920) configured to connect with the medical apparatus (335). The housing (920) is intended to be a holder or a means for configuring the adaptor-kit cartridge (330) in a frame that integrates with the hand-held (425) feature of the medical apparatus (335) and its purpose in that form of enabling a medical function. The housing may be a rectangular prism. It is acknowledged that there may be a minimum of at least two adaptor-kit cartridges, or a minimum of at least three adaptor-kit cartridges in alternative embodiments of the medical apparatus (335). In both cases, the Housing Step (2112) may further specify that at least one of the adaptor-kit cartridges enables a medical function selected from the group consisting of: cardiac defibrillation, cardiac pacing, and electrocardiography.

The Housing Step (2112) is supplemented by The Cartridge Housing Step (2005) which specifies framing each adaptor-kit cartridge (330) in a housing configured to connect with the medical apparatus, and wherein at least one of the adaptor-kit cartridges enables a medical function selected from the group consisting of: cardiac defibrillation, cardiac pacing, and electrocardiography.

In the method (100), the Choosing Step (115) is choosing the initial-state function, from one or more in the group consisting of: taking an ECG (835) of the person (420); measuring blood pressure (1105) within the person (420); measuring blood composition (1110) within the person (420); measuring body temperature (1115) of the person (420); measuring a heart rate (1120) of the person (420); measuring chest acceleration (1125) of the person (420) undergoing cardiopulmonary resuscitation (CPR); coaching (1130) in delivery of a medical function; performing automated external defibrillation of the person (420); installing an update (1141) to the firmware or software of the medical apparatus (335); performing a self-test (1143), which may be pre-programmed, of the medical apparatus (335); and providing status (1144) information about the medical apparatus (335). Certain initial-medical functions or initial-state functions may be chosen through a user-interface, automatically chosen by the medical apparatus (335), or both. The availability of functions may be dependent on functions enabled through one or more of an adaptor kit (1020).

When enabled, coaching involves advice using a speaker (1140), or other user interface (e.g., a screen) on the medical apparatus (335) or on a connected device, such as a smart phone.

The Choosing Step (115) is one that permits the person (420) to select a function preprogrammed and enabled for the medical apparatus (335). Preferably, the function may be selected from an option menu displayed on the medical apparatus (335) or screen that is integrated or connected thereto.

For the method (100), the accessories necessary to perform the initial-medical function are native to the medical apparatus (335), are provided with an adaptor kit (1020) when an adaptor-kit cartridge (330) is used, or are provided outside the adaptor kit (1020) when an adaptor-kit cartridge (330) is used.

For example, the function of measuring chest acceleration (1125) of the person (420) undergoing cardiopulmonary resuscitation (CPR) may be enabled by an inertial measurement unit (IMU) or an accelerometer within or attached to the medical apparatus (335). An IMU integrates multi-axes, accelerometers, gyroscopes, and other sensors to provide estimation of an object's orientation in space. Preferably, the inertial measurement unit measures 9 axes: 3 axes for acceleration, 3 for gyroscope, and 3 for magnetometer. Measurements of acceleration, angular rate, and attitude are typical data outputs. IMU inertial sensors are commonly used in dynamic motion measurements, payload platform stabilization, and antenna and camera pointing applications.

Figure 11:
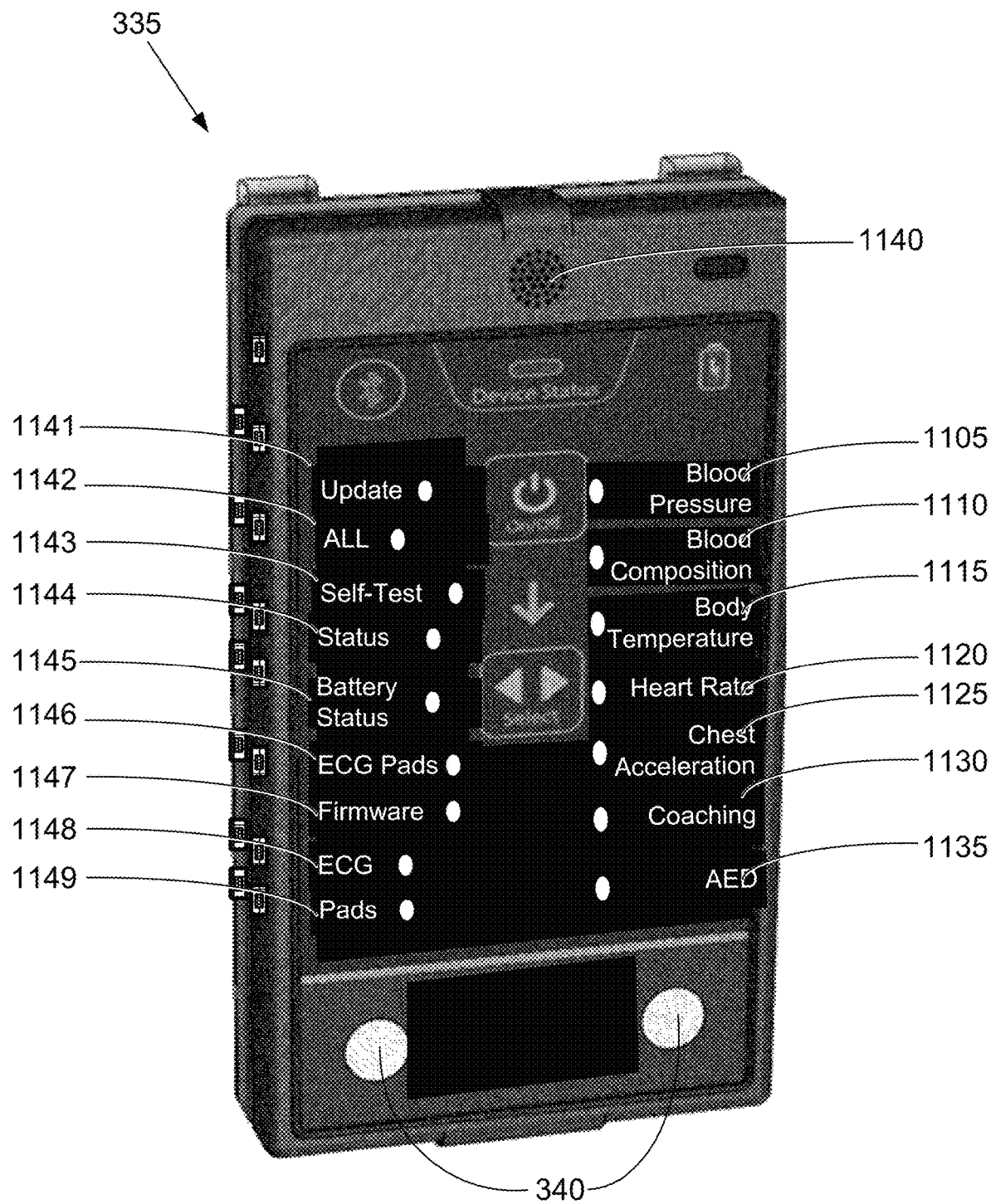
FIG. 11 illustrates a configuration of the medical apparatus that enables a user to select one or more of the optional initial-state and initial-medical functions of the medical apparatus.

As shown in FIG. 11, all of the selectable diagnostic medical functions may be elected by the selection of the "ALL" function. When "ALL" is selected, the medical apparatus (335) performs all of the selectable diagnostic medical functions, preferably in a pre-selected logical or sequential order. The selection of certain functions, such as self-tests, firmware or software updates, or providing medical apparatus (335) status may be automated.

The Selecting Step (120) includes optional steps in selecting the initial-medical function(s) or initial-state function(s). Examples include taking an ECG (835) of the person (420), identifying a need for an ECG (835) from the person (420), the person (420) having bare skin (820) accessible to at least two separated sensors (340), the at least two separated sensors (340) operationally connected to the medical apparatus (335); and touching the bare skin (820) to the at least two separated sensors (340). The bare skin (820) may be on a person's chest or arm, or when the ECG (835) is desired, the bare skin (820) is preferably on the person's fingers, as shown in FIG. 8. Selection may be automated or manual.

The Configuring Step (125) is configuring the at least two separated sensors (340) to be functional when the person (420) places a finger on each of the separated sensors, for example a left-hand thumb (806L) and a right-hand thumb (806R). Preferably, the medical apparatus (335) is configured to have the person (420) place a finger from each hand on one of the at least two separated sensors (340).

The Supplying Step (130) is an optional step of providing the medical apparatus (335) with multiple leads (345) configured for taking the ECG (835). Multiple leads (345) are superior to a single-lead because they offer multiple perspectives of the heart's activity from different angles.

The multiple leads (345) may be generated by using single wires with an attachment end that is placed on the person (420) or configured with one or more connector ends for electrical connection to the medical apparatus (335). These may also be multicore wires or cables that separate at one end for multiple attachments to the bare skin (820) of the person and have one or more connector ends for electrical connection to the medical apparatus (335).

Preferably, the multiple leads (345) are provided in a multicore wire that has multiple insulated conductors within a single jacketed cable as shown in FIG. 3. Preferably, the multiple leads (345) are configured to support 6, 12 or 15 lead ECGs. Additionally, the medical apparatus (335) may be configured to take the person's body temperature using the at least two separated sensors (340) or the multiple leads (345).

Modification Enabling New Medical Function

The method (100) identifies at least two specific adaptor kits in order to change or add one or more medical functions to the medical apparatus (335). Providing the wAED adaptor kit (710), the AED adaptor kit (610) and the ECG adaptor kit (1200) are optional steps in the method (100).

New Medical Function—AED

The AED-Adaptor Step (205) includes a step of providing an AED adaptor kit, the AED adaptor kit configured to enable the medical apparatus (335) to perform a new medical function of a reusable non-wearable external defibrillator (AED), the AED adaptor kit comprises: an AED cartridge; and disposable electrode pads.

Figure 6:
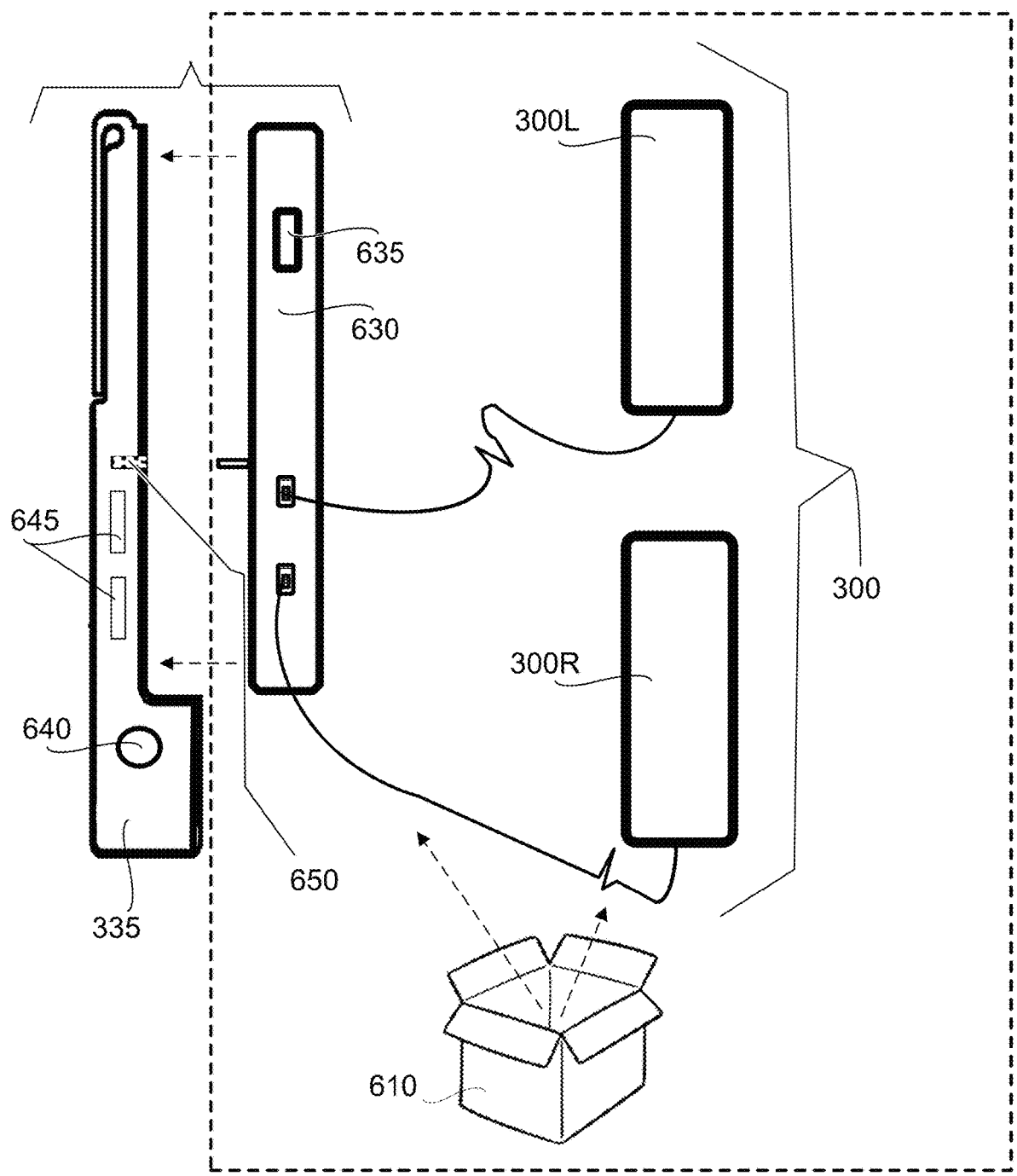
FIG. 6 illustrates the contents or minimum required components of an AED adaptor kit (within a dashed box) and also an exploded side view of the medical apparatus and AED cartridge configured for external defibrillation with a top view of two disposable-electrode pads.

The AED adaptor kit (610), shown within the dashed box in FIG. 6, comprises: an AED cartridge (630); and disposable-electrode pads (300), which are configured for external use and are the required accessories for this AED adaptor kit (610). Preferably, there are at least two of the disposable-electrode pads (300).

The AED adaptor kit (610) is configured to enable the medical apparatus (335) to perform a new medical function of an external defibrillator (AED). The AED adaptor kit (610) comprises: an AED cartridge (630) and disposable-electrode pads (300).

The AED adaptor kit (610) may support automated external defibrillation or manual external defibrillation, where the decision to shock is assessed by the user. Depending on the configuration, the AED adaptor kit (610) may be used for both automated and manual defibrillation when the accessories provided serve both functions. The AED adaptor kit (610) may be configured to support both adult and pediatric patients, or may be provided in an adult configuration and a different pediatric configuration.

Figure 18:
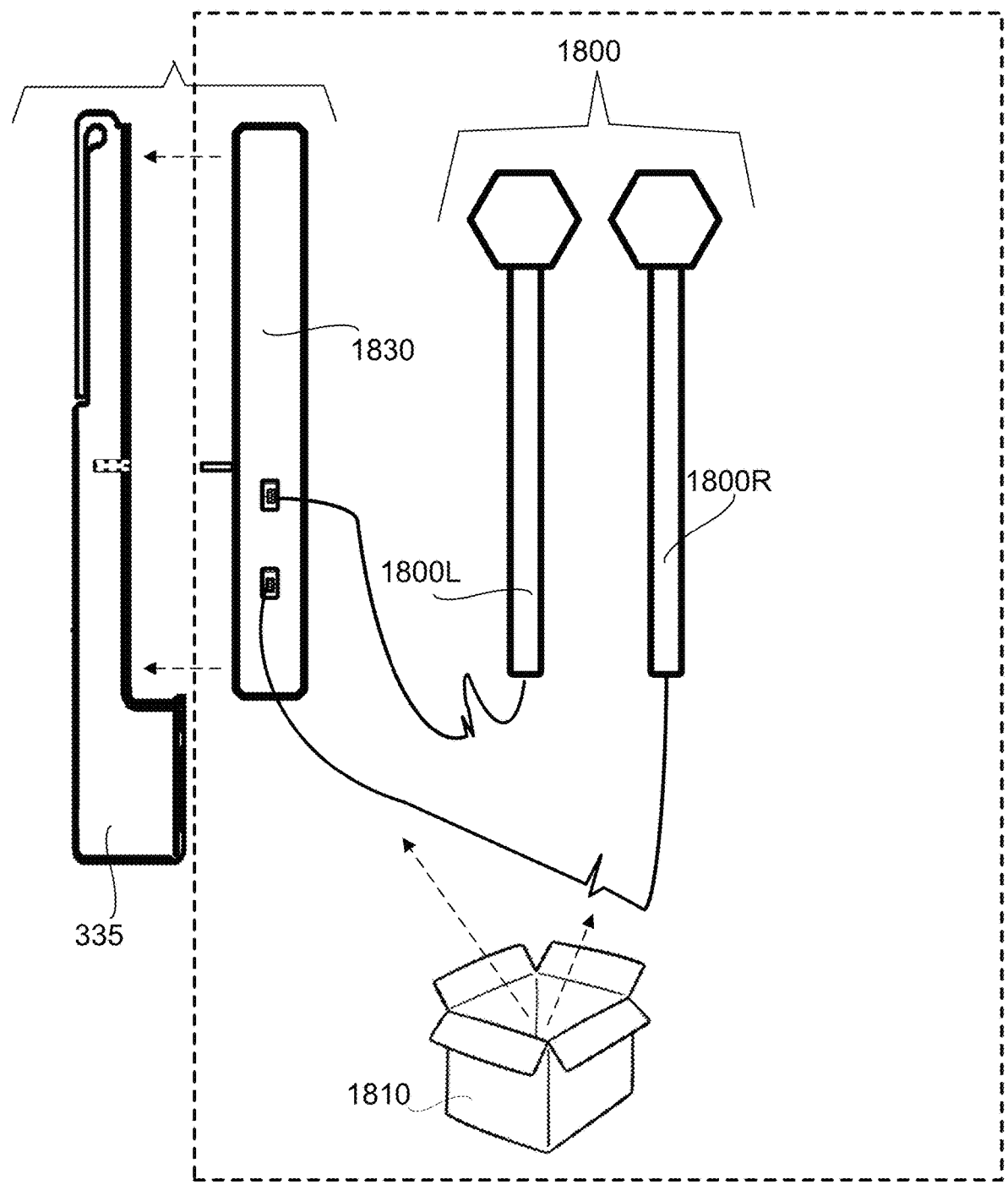
FIG. 18 illustrates the contents of an internal-defibrillation adaptor kit and the medical apparatus.
Figure 21:
FIG. 21 is a chart of steps in the method of using the medical apparatus.

The method (100) may include configuring the AED cartridge (630) to enable paddles (1025) for external defibrillation. The paddles (1025), also referred to herein as "electrodes," may be electrically connected to the AED cartridge (630), thereby allowing the paddles (1025) to be connected to the medical apparatus (335) when the AED cartridge (630) is attached. Each of the paddles (1025) includes an electrode surface for delivering therapeutic energy during defibrillation. Preferably, the paddles (1025) are interchangeable, as are the disposable-electrode pads (300). Any right or left designations, such as those shown in FIG. 8 and FIG. 18, are used herein for discussion purposes only and not to indicate a structural difference between them.

The AED-Connecting Step (215) includes providing an AED adaptor kit (610). The AED adaptor kit (610) is configured to enable the medical apparatus (335) to perform a second new medical function of a reusable non-wearable external defibrillator. This second new medical function is referred to herein as an AED.

The Storing-AED-Pads Step (220) is configuring the AED cartridge (630) to store each of the disposable-electrode pads (300) while each such disposable electrode pad is electrically connected to AED cartridge (630).

The AED cartridge (630) may be single-use. Each of the disposable-electrode pads (300) is preferably pre-wired to the AED cartridge (630) and need only be unpacked from the AED cartridge (630) and applied to the person (420) to enable defibrillation.

In a preferred embodiment for the AED cartridge (630), the AED cartridge (630) is designed to connect to the medical apparatus (335) using a variety of physical engagement mechanisms. These may include mechanical fasteners (e.g., clips, latches, bayonet fittings), magnetic couplings, keyed plug-in configurations, sleeve-style or overmating fits (where the cartridge fits partially over or into the housing), rails with locking detents, or snap-fit features. While sliding engagement is one option, it is not required, and other secure forms of physical and/or electrical attachment are contemplated. The overmating or sleeve-style engagement provides a more secure and simplified user interface for rapid deployment in emergency settings, reducing the risk of misalignment or incomplete insertion compared to sliding mechanisms. The connection mechanism is preferably robust enough to withstand use in emergency and field settings without accidental detachment, but easy enough to facilitate rapid exchange of the AED cartridge (630).

Added steps enabling use of the AED adaptor kit (610) include placing on the person (420) a left-disposable-electrode pad (300L) and a right-disposable-electrode pad (300R) from the plurality of AED disposable-electrode pads (300). The designations "left" and "right" are for description purposes only because there would typically be no physical or structural distinction between them.

Preferable placement of the disposable-electrode pads (300) is generally as shown in FIG. 9. Each of the disposable-electrode pads (300) is attached to bare skin (820) at designated areas (which are preferably at center chest and back, a person's right upper quadrant under the collar bone and a person's left middle side, or any other place that facilitates a therapeutic charge (915) delivered for defibrillation of the heart). Placement on the front and back of the person (420) may be used in accordance with standard practices sometimes relating to the age of the person undergoing defibrillation.

The AED-Connecting Step (215) optionally includes a step of connecting the AED cartridge (630) to the medical apparatus (335) to enable its operation; and placing on the person (420) two of the disposable-electrode pads (300).

Example of an AED Adaptor Kit

An example of an AED adaptor kit includes an AED cartridge (630) that also stores at least two of the disposable-electrode pads (300) that are directly wired to the AED cartridge (630). Once the AED cartridge (630) is connected to the medical apparatus (335), the disposable-electrode pads (300) are also connected to the medical apparatus (335).

In this example, to utilize the AED adaptor kit (610), after connecting the AED cartridge (630) to the medical apparatus (335), a user opens the AED cartridge (630) to access two disposable-electrode pads by taking off a back cover or peeling off a seal on the AED cartridge (630). Then the user removes the disposable-electrode pads (300) and applies them to the person (420). The disposable-electrode pads (300) are electrically connected to the AED cartridge (630).

In other embodiments, replacement disposable-electrode pads are provided and these simply plug into the AED cartridge (630) or plug into the medical apparatus (335). Accordingly, a disposable-electrode pad may be electrically connected either directly to the medical apparatus (335) or indirectly through the adaptor-kit cartridge, depending on the configuration. Both connection types are contemplated within the scope of the adaptor kit and its use with the medical apparatus (335). When used in combination with the AED adaptor kit (610), the medical apparatus (335) contains the necessary electronics to provide a therapeutic charge (915) for defibrillation.

Optionally, the AED cartridge (630) employs an external battery to ensure that adequate power is available for defibrillation using the disposable-electrode pads (300).

Optionally, the medical apparatus (335) offers a lower power sleep mode to conserve power, waking up from low power mode to enter an initial-state.

New Medical Function—Internal-Defibrillation

The method (100) may include an Internal-Defibrillation Step (1720), which is Related to the AED-Adaptor Step (205) in that both the AED-Adaptor Step (205) and the Internal-Defibrillation Step (1720) involve heart defibrillation of a person (420). The Internal-Defibrillation Step (1720) includes a step of providing an internal-defibrillation adaptor kit (1810). The internal-defibrillation adaptor kit (1810) includes an internal-defibrillation cartridge (1830) and internal-defibrillation paddles (1800) configured for internal defibrillation. Internal refers to inside the body with physical contact with the person's heart.

Internal defibrillation is enabled when internal-defibrillation paddles (1800) are placed directly on an exposed heart of the person (420) undergoing open chest surgery. Shown in FIG. 18 is a left-internal-defibrillation paddle (1800L) and a right-internal-defibrillation paddle (1800R). There is no structural difference between the left and the right paddles. Preferably, the internal-defibrillation adaptor kit (1810) includes internal-defibrillation paddles (1800) that can be autoclaved.

The Internal-Defibrillation Step (1720) further includes steps of: connecting the internal-defibrillation cartridge to the medical apparatus (335) to enable manual defibrillation; connecting the internal-defibrillation paddles (1800) to the medical apparatus (335) through the internal-defibrillation cartridge (1830); and placing the internal-defibrillation paddles (1800) directly onto a person's heart for defibrillation.

When the Internal-Defibrillation Step (1720) includes internal-defibrillation paddles (1800) that are pre-wired to the internal-defibrillation cartridge (1830) as an accessory (1015) in the internal-defibrillation adaptor kit (1810), then the method (100) preferably includes a Pre-Connected Paddles Step (1725).

The Initial-State Step (1920) includes the step of setting an initial-state function of the medical apparatus (335) by connecting to the medical apparatus (335) an adaptor-kit cartridge (330) prior to activating the medical apparatus (335). More than one adaptor-kit cartridge may be pre-connected to the medical apparatus (335). This step ensures an intended medical function is available to, or can be activated for, the medical apparatus (335) when an adaptor-kit cartridge (330) is pre-installed on the medical apparatus (335) and the medical apparatus (335) enters an initial-state.

The Pre-Connected Paddles Step (1725) may include a step of providing an internal-defibrillation adaptor kit (1810). The internal-defibrillation adaptor kit (1810) includes an internal-defibrillation cartridge (1830) and internal-defibrillation paddles (1800) that are pre-connected to the internal-defibrillation cartridge (1830). The internal-defibrillation paddles (1800) are configured for internal defibrillation, typically with open-chest surgery and an exposed heart. The Pre-Connected Paddles Step (1725) further includes a step of connecting the internal-defibrillation cartridge (1830) to the medical apparatus (335) to enable manual defibrillation; and placing the internal-defibrillation paddles (1800) directly onto a person's heart for defibrillation.

The method (100) may include a Pre-Connected Paddles Step (1725), which also enables use of the internal-defibrillation adaptor kit (1810) for internal (or open chest) heart defibrillation, except that the left-internal-defibrillation paddle (1800L) and the right-internal-defibrillation paddle (1800R) are pre-wired, i.e. preconnected, to the internal-defibrillation cartridge (1830). When the left-internal-defibrillation paddle (1800L) and the right-internal-defibrillation paddle (1800R) are pre-connected to the internal-defibrillation cartridge (1830), the method (100) includes a step of connecting the internal-defibrillation cartridge (1830) to the medical apparatus (335); and placing the internal-defibrillation paddles (1800) directly onto a person's heart for defibrillation.

New Medical Function—wAED

The wAED-Adaptor Step (221) includes providing a wAED adaptor kit (710), the wAED adaptor kit (710) is configured to enable the medical apparatus (335) to perform a new medical function of a wearable automated external defibrillator (wAED), the wAED adaptor kit (710) comprises a wAED cartridge (730) configured to attach to, and operationally integrate with, the medical apparatus (335); and disposable-electrode pads (300). Optional steps in addition to the wAED-Adaptor Step (221) are the wAED-Harness Step (222) and the wAED Implementation Step (223).

The wAED-Harness Step (222) requires the wAED adaptor kit (710) to include a harness (405) and includes a step of attaching the disposable-electrode pads (300) to the person (420).

The wAED Implementation Step (223) adds additional steps of connecting the wAED cartridge (730) to the medical apparatus (335); and attaching the disposable-electrode pads (300) to the person (420).

The method (100) of using the medical apparatus (335) may include a wAED-Adaptor Step (221) and a wAED-Connecting Step (1325). With these steps, the method (100) provides the medical apparatus (335) with the wAED adaptor kit (710) so that the medical apparatus (335) may be converted to a wAED.

The wAED-Adaptor Step (221) includes multiple steps of providing a wAED adaptor kit configured to enable the medical apparatus (335) to perform a new medical function of a wearable automated external defibrillator (wAED), the wAED adaptor kit comprises a wAED cartridge (730) configured to attach to, and operationally integrate with, the medical apparatus (335)

Optional added steps to the wAED-Adaptor Step (221) are: a Storing-wAED-Pads Step (1320) configuring the wAED adaptor kit (710) to store disposable electrode pads; a wAED-Harness Step (222) for including a harness (405) in the wAED adaptor kit (710) and adding a step of securing the harness (405) on a person (420); and a wAED-Connecting Step (1325) adding steps of: connecting the wAED cartridge (730) to the medical apparatus (335); and adding a step of attaching two disposable electrode pads to the person (420).

Figure 7:
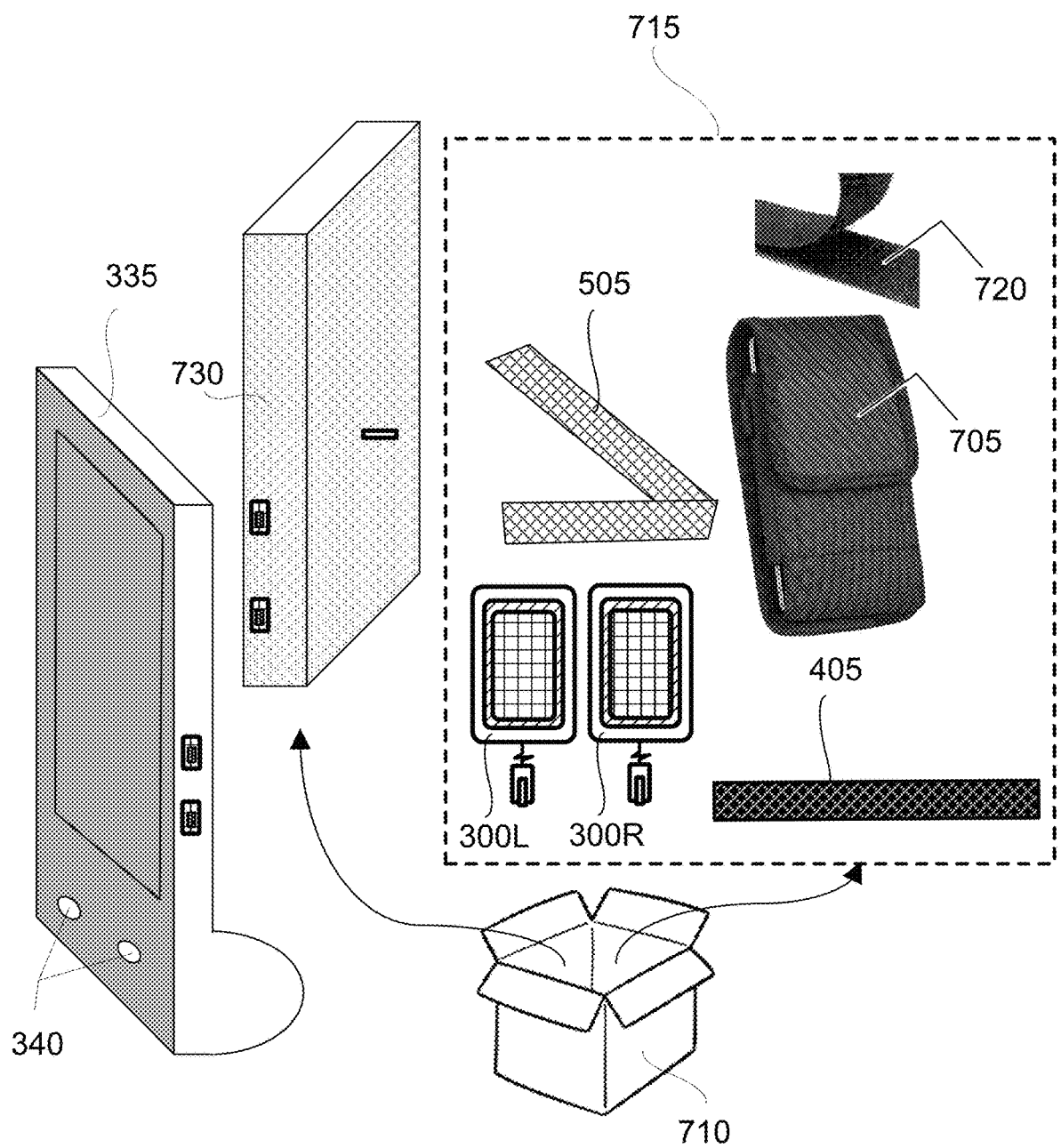
FIG. 7 illustrates potential contents or components of an adaptor kit for the wAED, including a harness.

FIG. 7 illustrates contents or components of a wAED adaptor kit (710) to enable altering the medical apparatus (335) to perform the new medical function of a wearable automated external defibrillator. The wAED adaptor kit (710) includes wAED cartridge (730) and may optionally include a harness (405) and disposable-electrode pads (300).

The wAED cartridge (730) attaches to, and operationally integrates with, the medical apparatus (335). In a preferred embodiment, the medical apparatus (335) allows the person (420), that is the patient, to take an ECG preferably using four electrodes two of which are the disposable-electrode pads (300) (also known as patches). In this implementation, the other two electrodes are the at least two separated sensors (340) on the medical apparatus (335). The at least two separated sensors (340) are surface electrodes or tabs that are accessible to the fingers or hands of the user on an external surface of the medical apparatus (335). The left hand (821L) of the person (420) and the right hand (821R) of the person (420) are shown in FIG. 8. Finger examples are also shown in FIG. 8 as a left-hand thumb (806L) and a right-hand thumb (806R). Additional surface electrodes may be on the wAED cartridge (730), which may be laid on the bare skin (820) of the person (420).

The wAED adaptor kit (710) may include a harness (405). When included, the harness (405) is configured to be worn by the person (420) and may route wires from the disposable wAED electrode pads to the medical apparatus (335). The harness (405) is an accessory (1015) in the wAED adaptor kit (710) that is defined herein to include a belt, as shown in FIG. 4; a shoulder rig (505) as shown in FIG. 5 or as in any other shoulder belting arrangement; a clip attachment (705) usable on the clothing or belt of a person; a hook-and-loop strip (720) attached or attachable to the person or to the person's belt or to other clothing worn by the person; and any other device-holding mechanism for use on a person or a person's clothing.

When included in the wAED adaptor kit (710), the harness (405) preferably includes a connecting wire (350) that may be embedded in the harness (405), a connecting wire (350) may also be provided as a separate or backup accessory. In either case, the harness (405) provides a convenient organizing function for the wires to establish an electrical connection between the disposable-electrode pads (300) and the wAED cartridge (730) and/or the medical apparatus (335).

Harness Examples

Figure 4:
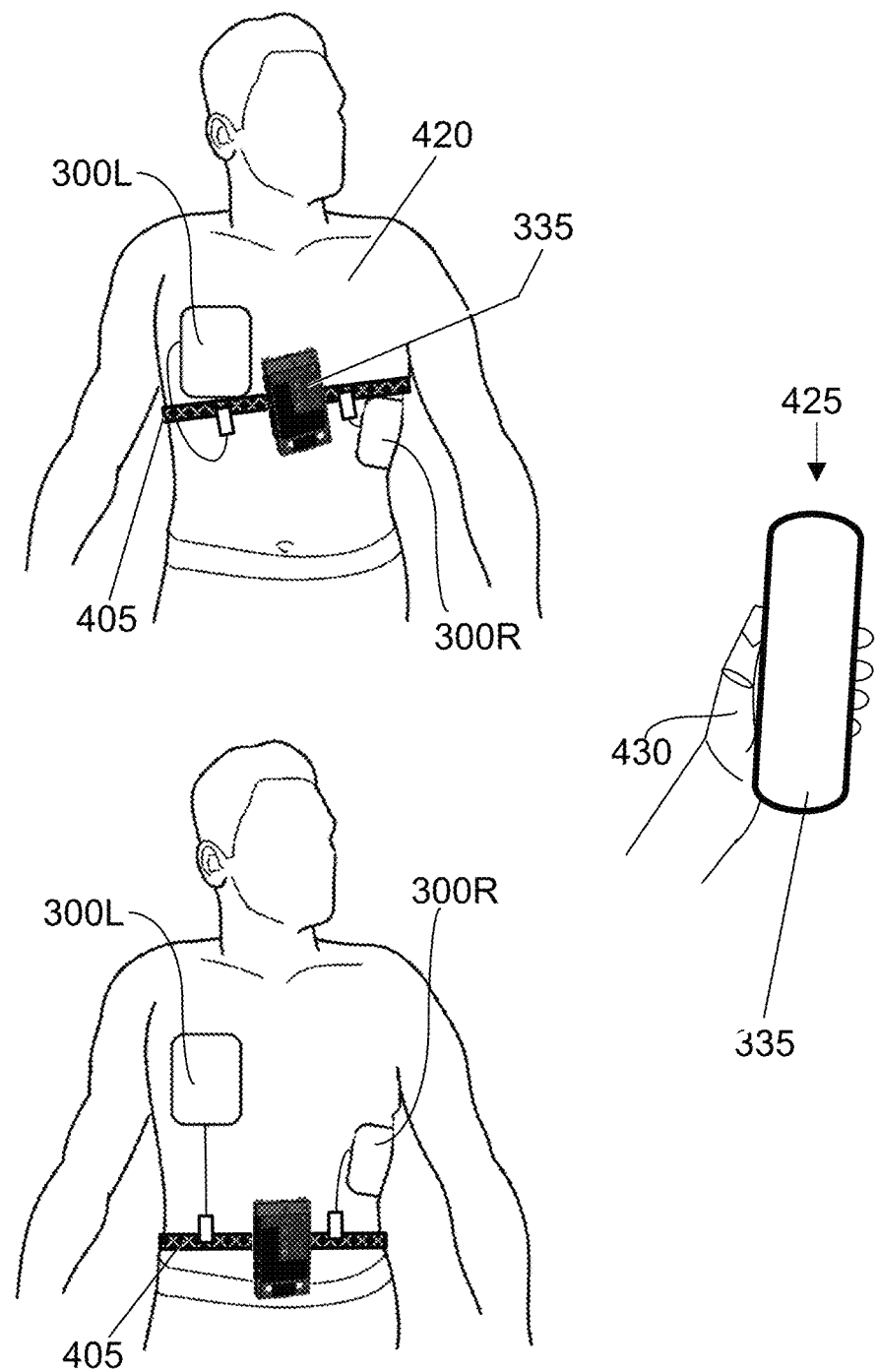
FIG. 4 shows two frontal views of a person with two different types of harnesses securing the medical apparatus with a wAED cartridge and further showing two disposable-electrode pads in approximate position for use and further showing the hand-held feature of the medical apparatus.
Figure 5:
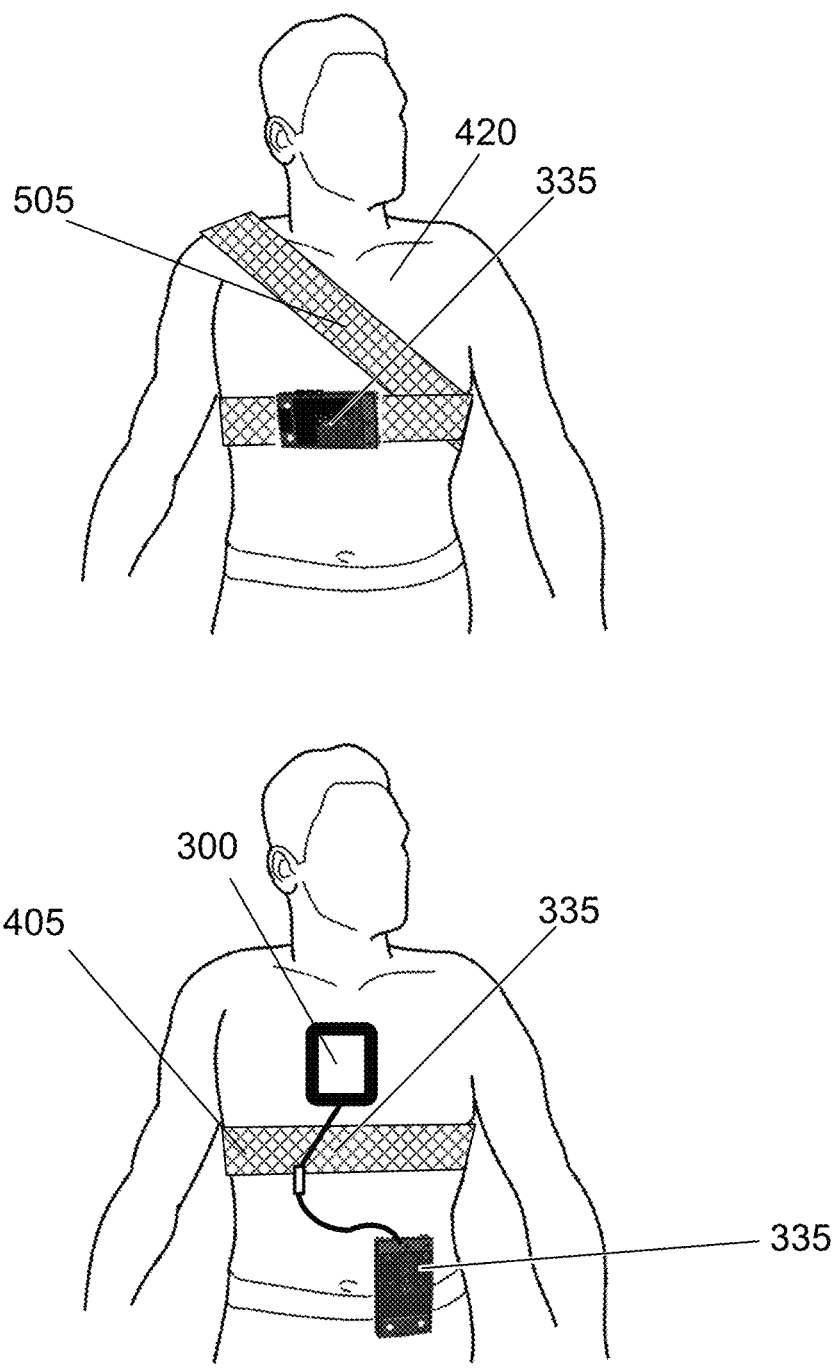
FIG. 5 shows two frontal views of a person with two potential configurations of the harness and two different locations for attachment of a medical apparatus connected to a wAED cartridge.

Examples of securing the harness (405) to the person (420) are illustrated in FIG. 4 and FIG. 5 showing a harness (405) and a harness that is a shoulder rig (505) that is supported by one shoulder. Examples in FIG. 4 and FIG. 5 show the harness (405) surrounding the person's waist and chest. The lower illustration of the person without a shoulder rig (505) has an arrangement of one of the disposable-electrode pads (300) on the front and one of the disposable-electrode pads (300) on the back (not shown) of the person (420).

wAED and AED Accessories

In FIG. 7, the rectangular dashed box illustrates accessories, including exemplary embodiments of the harness (405), as illustrated in FIGS. 4, 5 and 7. These examples of the harness (405) are referred to herein as harness (405), shoulder rig (505), clip attachment (705), and hook-and-loop strip (720).

The harness (405) is preferably included in the wAED adaptor kit (710). Optionally, the harness (405) in any embodiment may incorporate the wAED cartridge (730), so that once the harness (405) is plugged into the medical apparatus (335), no separate wAED cartridge is required. For this implementation, the wAED cartridge (730) is physically available within one of these embodiments.

Preferably, each of the disposable-electrode pads (300) includes an electrical wire (319) that terminates in a plug (320). The plug (320) is configured to attach to a mating plug (325) on a connecting wire (350) to the wAED cartridge (730) or to the medical apparatus (335). The electrical wire (319) or connecting wire (350) may run through the harness (405). The plugs may be male or female on one or the other end of the wire as long as they are configured to mate with the connecting plug. The connecting wire (350) is optionally part of the wAED adaptor kit (710) or may be provided as a separate component.

Each of the disposable-electrode pads (300) and any wires that are riveted or otherwise permanently attached to each of the disposable-electrode pads (300) are configured to be disposable after one or more uses. Preferably, the adaptor-kit cartridge (330) that is used in the method (100) is configured for reuse without any need for replacement after a first or any subsequent use for the new medical purpose.

The harness (405) is preferably configured to be reusable but replaceable after it is worn out. In one embodiment, the clip attachment (705) is a clip on the back of the wAED cartridge (730).

The harness (405) is further configured for facilitation of a wired connection of each of the disposable-electrode pads (300) to the wAED cartridge (730). It is preferred that there be at least two such wired connections in a typical use of the wAED (one for each pad): a connection from a left-disposable-electrode pad (300L) and one from a right-disposable-electrode pad (300R). The right and left designations are only for convenience of describing them because there is typically no other distinguishing feature between a left and right disposable-electrode pad.

Such facilitation from the harness (405) may preferably include connecting with each electrical wire (319) from two wAED disposable-electrode pads used on a person (420) in a typical implementation using the wAED adaptor kit (710), as shown in FIG. 9. The harness (405) may be configured to comfortably conceal and hold the medical apparatus (335) with the wAED cartridge (730) attached.

Also, such facilitation may include concealing and routing each connecting wire (350), each plug (320), and each mating plug (325) from each of the disposable-electrode pads (300) to the wAED cartridge (730). A hook and loop fastener or a belt clip on the cartridge or medical apparatus (335) are examples of tools to hold the medical apparatus (335) with the wAED cartridge (730) attached. The medical apparatus (335) with the wAED cartridge (730) attached may also be stored in the person's clothing or carried in a person's pocket. When a mating pair of plug-in connectors is used: one on each end of the connecting wire (350) from the wAED cartridge (730) and one on the electrical wire (319) connecting to each of the disposable-electrode pads (300).

These optional steps in the method (100) are referred to in FIG. 2 as a wAED-Adaptor Step (221), a wAED-Harness Step (222), a wAED Implementation Step (223), and an ECG Adaptor Step (225).

The AED-Adaptor Step (205) includes providing an AED adaptor kit (610). The AED adaptor kit (610) is configured to enable the medical apparatus (335) to perform a new medical function of a reusable non-wearable external defibrillator. The reusable non-wearable external defibrillator is referred to herein as an AED and is shown in FIG. 6

The AED adaptor kit (610) includes an AED cartridge (630) and an AED accessory (715). There is preferably at least one accessory in the AED adaptor kit (610), including at least two of the disposable-electrode pads (300), which may be referred to herein as a plurality of disposable-electrode pads. In an alternative embodiment, the disposable-electrode pads (300) may be provided in packaging supplemental to the AED adaptor kit (610). Each of the disposable-electrode pads (300) is exemplified in FIG. 3 within the dashed box.

For the method (100), the Initial-State Using Step (1408) includes using the medical apparatus (335) to perform at least one initial-state function. The use of the medical apparatus (335) may be pre-programmed, allowing such use to be automated, or may involve interaction with a medical apparatus (335) operator through a user interface.

The present disclosure teaches a preferable configuration for the disposable-electrode pads (300) used with the wAED configuration that enables daily use by the person (420). Preferably, each of the disposable-electrode pads (300) that is disclosed herein is stored in a sealed package. Preferably, each of the disposable-electrode pads (300) would be sealed separately, but a plurality of such disposable-electrode pads may also be sealed together in the same package. Preferably, the disposable-electrode pads (300) would be purchased (via prescription in some countries) in a box with a large number of sealed patches. Each of the disposable-electrode pads (300) is configured to be worn throughout the day or night. FIG. 3 illustrates a bottom view (sticky side up) of a preferred disposable electrode pad as it might look when taken out of a package prior to placement on the bare skin (820) of a person (420).

While similar to electrode pads used by public access automated external defibrillators on the market today, each of the disposable-electrode pads (300) is different in that each of the disposable-electrode pads (300) is configured to be worn throughout the day, similar to how one might where a dermal patch designed to deliver medication, like a nicotine patch used as a substitute for cigarette smoking. Like all dermal patches, each of the disposable-electrode pads (300) is preferably not configured for reuse once removed from the bare skin (820) of the person (420), either on the person (420) or on another patient. Depending on the embodiment of the harness, each of the disposable-electrode pads (300) is configured may be placed under, or partially under, the harness (405) at least as often as the person (420) removes or dons the harness (405).

Each of the disposable-electrode pads (300), like a dermal patch, is essentially a stand-alone dermal sticker. Each of the disposable-electrode pads (300) for a wAED adaptor kit (710) taught herein is preferably not the usual AED electrode pad because each of the disposable-electrode pads (300) is configured to be worn for long durations, e.g. preferably up to a full day or longer.

Each of the disposable-electrode pads (300) is exemplified in FIG. 3. Each of the disposable-electrode pads (300) for a wAED adaptor kit (710) is typically attached to a connecting wire (350) that is the interface between the person and the adaptor-kit cartridge (330), enabling the medical apparatus (335) to analyze the heart's rhythm and deliver electric charge to restore standard heartbeat patterns.

The disposable-electrode pads (300) preferably include: a skin adhesive (305) (e.g., hydrogel or pressure sensitive adhesive); and one or more conductive elements (315) (e.g., hydrogel, carbon-loaded vinyl, tin, or silver). Preferably, each of the disposable-electrode pads (300) includes: an optimized formulation of hydrogel that serves as a conductive agent and an aid in adhering each of the disposable-electrode pads (300) to the person's skin. Preferably, the skin adhesive (305) is a pressure sensitive adhesive that supports day-long adhesion and helps retain electrical conductivity while being worn by the person (420).

The Storing-AED-Pads Step (220) is a step of providing the disposable-electrode pads (300); electrically connecting the disposable-electrode pads (300) to the medical apparatus (335) and further configuring the AED adaptor kit (610) to store the disposable-electrode pads (300) while each such disposable electrode pad is electrically connected to the AED cartridge (630).

Preferably, each of the disposable-electrode pads (300) is the same size. Pad size would preferably comply with the International Electrotechnical Commission (IEC) standard for Medical electrical equipment—Part 2-4: Particular requirements for the basic safety and essential performance of cardiac defibrillators IEC 60601-2-4. This IEC standard sets forth requirements for the basic safety and essential performance of cardiac defibrillators. According to this IEC standard, the minimum area of each of the electrodes, one of which is part of, or attached, to each patch, must be 50 cm$^2$ for adult external use and 15 cm$^2$ for pediatric external use. Together, the total active (gel) area for two disposable-electrode pads would be at least 150 cm$^2$ for adults and 45 cm$^2$ for children, but preferably would have a larger active gel area.

The AED-Connecting Step (215) includes multiple actions comprising: connecting the AED cartridge (630) to the medical apparatus (335) to enable its operation; and placing on the person (420) two of the disposable-electrode pads.

An example of a typical placement of two of the disposable-electrode pads (300) on an adult is illustrated in FIG. 4. A left-disposable-electrode pad (300L) and a right-disposable-electrode pad (300R) are shown in FIG. 4.

The method (100) of using the medical apparatus (335) optionally includes the AED-Connecting Step (215), the AED-Adaptor Step (205), and the Storing-AED-Pads Step (220). The added steps include: providing an AED adaptor kit (610), the AED adaptor kit (610) configured to enable the medical apparatus (335) to perform a second new medical function of a reusable non-wearable external defibrillator (AED), the AED adaptor kit (610) comprises: an AED cartridge (630); and disposable-electrode pads (300); connecting the AED cartridge (630) to the medical apparatus (335) to enable its operation; and placing on the person two of the disposable-electrode pads (300); providing the disposable-electrode pads (300); electrically connecting the disposable-electrode pads (300) to the medical apparatus (335) and further configuring the AED adaptor kit (610) to store the disposable-electrode pads (300) while each such disposable-electrode pad is electrically connected to the AED cartridge (630).

The Storing-AED-Pads Step (220) include steps of providing the disposable-electrode pads (300); electrically connecting the disposable-electrode pads (300) to the medical apparatus (335) and further configuring the AED adaptor kit (610) to store the disposable-electrode pads (300) while each such disposable electrode pad is electrically connected to the AED cartridge (630).

The AED-Connecting Step (215) includes steps of connecting the AED cartridge (630) to the medical apparatus (335); and placing on the person (420) two of the disposable electrode pads; and electrically connecting the disposable-electrode pads (300) to the medical apparatus (335) either directly or through the AED cartridge (630).

The harness (405) is further configured to hold the medical apparatus (335) with the wAED cartridge (730) attached thereto. As with all adaptor-kit cartridges (330), the wAED cartridge (730) operationally integrates with the medical apparatus (335). A hook and loop fastener, a clip attachment (705), a pocket or a slot are potential attachment mechanisms.

The wAED-Harness Step (222) further includes a step of securing the harness (405) to the person (420). Examples of the harness (405) are illustrated in FIG. 4 and FIG. 5 showing a harness (405) or a shoulder rig (505) that is supported by one shoulder. As an example, the harness (405) may surround the person's waist or chest, as illustrated in FIG. 4 and FIG. 5, respectively.

To extend the life of the wAED, an external battery is optionally embedded in the harness (405). The external battery may be electrically connected but detached and apart from the harness (405). Alternatively, a battery may be present in the wAED cartridge (730) that connects to the harness (405). Alternatively, an external battery may be mounted on the medical apparatus (335). The battery may be rechargeable or non-rechargeable.

Detecting and alerting the person (420) when any disposable-electrode pads (300), also referred to as a patch, should be changed: Preferably, a timely recommendation to the person (420) to change each of the disposable-electrode pads (300) is initiated by measuring the resistance between the left-disposable-electrode pad (300L) and the right-disposable-electrode pad (300R). When the resistance drops to a pre-determined threshold, the person (420) is alerted to change the patches. Software or firmware within the medical apparatus (335) or within the wAED cartridge (730) may be programmed to use a timer to alert the person (420) when it is recommended to replace the disposable-electrode pads.

Firmware, as used herein, is software that provides low-level control of computing device hardware. Firmware may control and perform monitoring and data manipulation functionality.

Preferably, the wAED cartridge (730) interfaces with the medical apparatus (335) and the medical apparatus (335) includes a wireless communication capability to provide near-real time telemetry of patient conditions. Such telemetry may include a speaker (1140) and screen or user interface. Preferably, the screen, speaker, or user interface includes a visual or audible alert and ability to cancel before an electric charge is delivered from the medical apparatus (335) with the wAED cartridge (730) attached. Preferably, telemetry is also used for analysis of the person's heart activity and to predict heart failure.

Preferably, the medical apparatus (335) with the wAED cartridge (730) attached is configured to wirelessly communicate with a smartphone or a smart tablet, for example using BLUETOOTH. The medical apparatus (335) with the wAED cartridge (730) attached may have cellular telephone capability. Preferably, the medical apparatus (335) with the wAED cartridge (730) attached includes a speaker (1140).

Preferably, the medical apparatus (335) with the wAED cartridge (730) attached has a cellular or a wi-fi chip to transmit ECG telemetry directly to a provider or to the cloud. Optionally, the medical apparatus (335) with the wAED cartridge (730) attached tethers to a smart device to enable telemetry transmission. Optionally, the medical apparatus (335) with the wAED cartridge (730) attached has a video interface. The medical apparatus (335) with the wAED cartridge (730) attached optionally has a non-video interface and is configured to utilize a video and speaker from a smart device, such as a cell phone (i.e., smartphone).

Third New Medical Function

Figure 12:
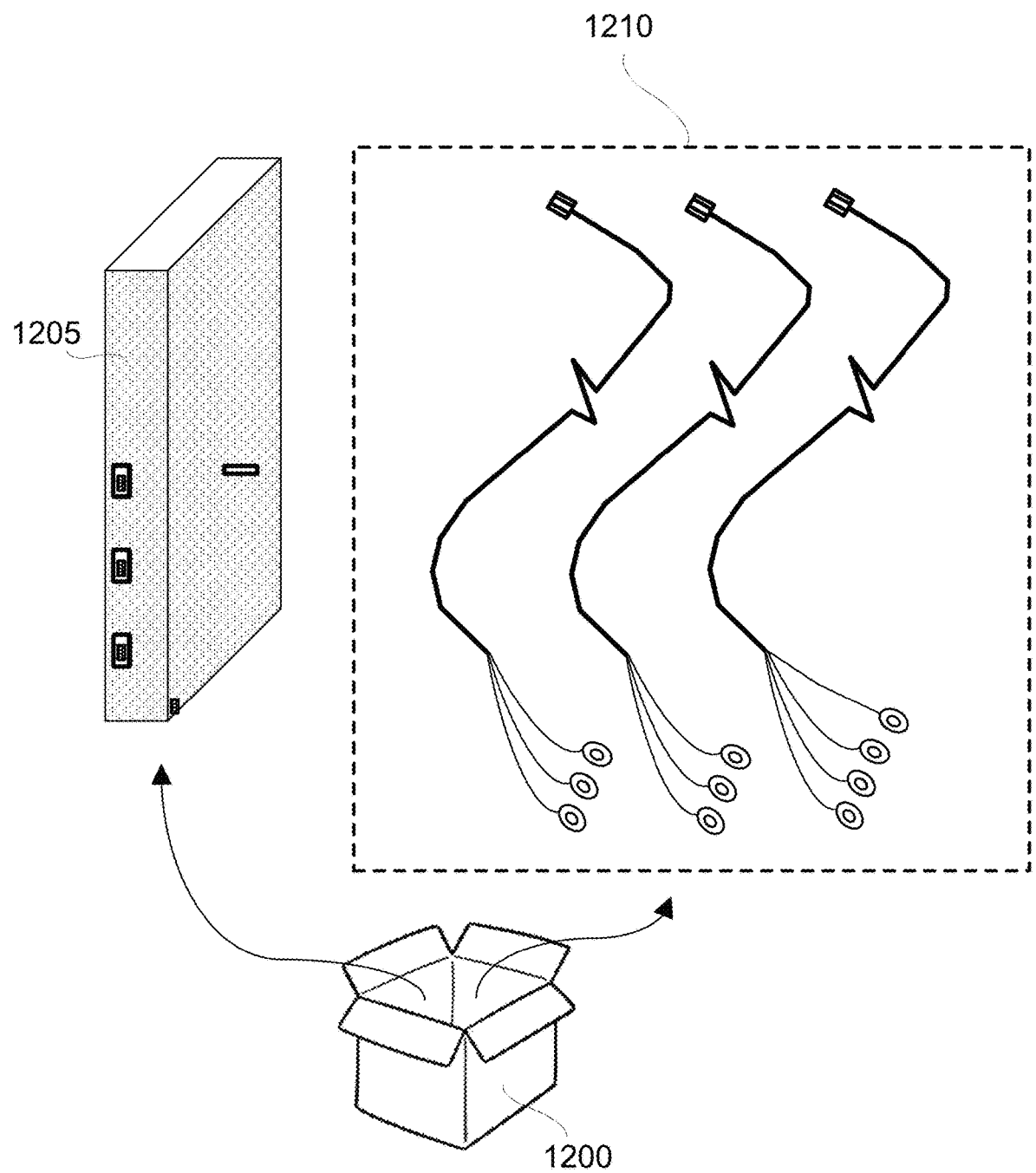
FIG. 12 illustrates the contents of an ECG adaptor kit for performing an electrocardiogram.
Figure 15:
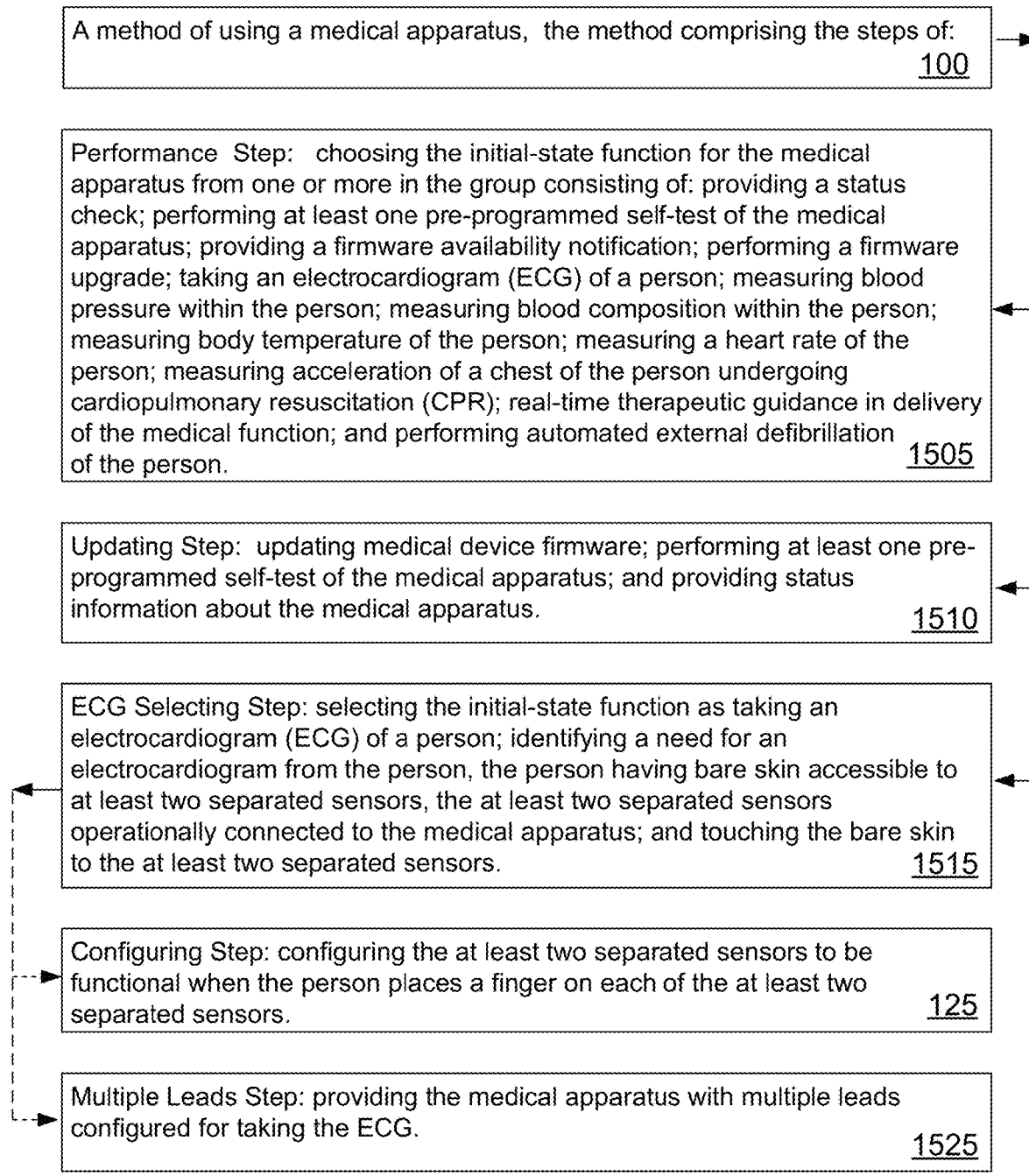
FIG. 15 is a chart of optional steps for the method of using the medical apparatus.

The ECG Adaptor Step (225) includes providing an ECG adaptor kit (1200), the ECG adaptor kit (1200) is configured to enable the medical apparatus (335) to perform a third new medical function of taking an electrocardiogram (ECG), this third adaptor kit comprises: an ECG adaptor-kit cartridge (1205); and a plurality of sensors (1210), preferably at least 12 sensors, configured to measure the magnitude and direction of electrical currents in a heart during each heartbeat. The plurality of sensors (1210) is shown within the dashed box in FIG. 12.

Alternative Medical Function Embodiments

The AED Step (1306) is enabling the medical apparatus (335) to perform a new medical function of a reusable non-wearable automated external defibrillator, also referred to herein as an AED.

The AED-Providing Step (1310) includes steps of: providing an AED adaptor kit (610) configured to enable the medical apparatus (335) to perform a new medical function of a reusable non-wearable external defibrillator (AED), the AED adaptor kit (610) comprising: an AED cartridge (630); and disposable-electrode pads; connecting the AED cartridge to the medical apparatus (335) to enable its operation; and placing on the person two of the disposable-electrode pads (300).

The AED-Functioning Step (1305) is connecting the AED cartridge (630) to the medical apparatus (335) to enable its operation; and placing on the person (420) two of the disposable-electrode pads (300).

The medical apparatus (335) starts out with an initial-state function, which is distinguished from the initial-medical function because the initial-state function may be more or less than a medical function (for example, it may be a medical apparatus (335) status (1144) check, a self-test (1143), which may be pre-programmed, or provide coaching (1130)). The selection of certain initial-state functions, such as self-tests, firmware or software updates, or providing medical apparatus (335) status may be automated.

The Apparatus-Providing Step (1405) is a step of providing a medical apparatus (335) configured to be hand-held (425) and further configured to perform an initial-state function. The initial-state function is selected from the group consisting of an updating sequence and a medical function. The medical apparatus (335) is further configured to be transformed to enable performance of at least two different medical functions when modified using at least two adaptor kits that enable different medical functions.

The Second-Apparatus-Providing Step (2105) is nearly the same as the Apparatus-Providing Step (1405) except that it involves transformation of the medical apparatus (335) using at least three adaptor kits and requires configuring the medical apparatus (335) to be hand-held (425) and also configured to perform an initial-state function. The initial-state function may include one of an updating sequence and a medical function. The medical apparatus (335) is further configured to be transformed to enable performance of a plurality of different medical functions when modified using at least three adaptor kits, where each of the three adaptor kits provides a different medical function.

Medical functions include, but are not limited to, administering a defibrillation shock with a hand-held Automatic Electronic Defibrillator (AED), taking an ECG of a person, and using a wearable Automatic Electronic Defibrillator. As used herein, a 'medical function' refers to a diagnostic, therapeutic, or monitoring capability performed on a person (420). Instructional or training modes, including AED simulation or CPR training, are not considered medical functions, but may be included as initial-state functions.

The method (100) may include a Hand-Held Step (1905), which includes the step of configuring the hand-held (425) feature of the medical apparatus (335) to be suitable to be held in a single adult hand (430) while being used. The Hand-Held Step (1905) may be supplemented by the Size-Limiting Step (1915). The Size-Limiting Step (1915) includes a step of limiting the weight of the medical apparatus (335) to less than 0.75 kilograms; and a step of confining the longest dimension of the medical apparatus (335) to a maximum of 16.5 centimeters. The Size-Limiting Step (1915) is optional and when implemented is intended to limit the medical apparatus (335) to a weight and size that maintain ease of use in potential portable applications.

The Kit-Providing Step (1406) is providing the at least two adaptor kits, each adaptor kit (1020) in the at least two adaptor kits comprises an adaptor-kit cartridge (330) configured to use an accessory (1015), which, when the adaptor-kit cartridge (330) is operationally integrated with the medical apparatus (335), this operational integration together with use of the accessory (1015) enables operability of the medical apparatus (335) to perform the new medical function enabled by that adaptor kit (1020).

The Accessory-Providing Step (1407) is providing the accessory (1015). This is the accessory (1015) for which the adaptor-kit cartridge (330) is configured in the Kit-Providing Step (1406).

The Second Kit-Providing Step (2106) relates to the use of at least three adaptor kits and an accessory (1015) instead of the at least two adaptor kits and an accessory (1015) in the Kit-Providing Step (1406). The Second Kit-Providing Step (2106) includes a step of providing the at least three adaptor kits, each of the adaptor kits, in the at least three adaptor kits, comprises an adaptor-kit cartridge (330) configured to use an accessory (1015), which, when the adaptor-kit cartridge (330) is operationally integrated with the medical apparatus (335), this operational integration together with use of the accessory (1015) enables operability of the medical apparatus (335) to perform the new medical function enabled by that adaptor kit (1020).

The providing steps noted above provide one or more accessories (1015) required to perform the new medical function. The accessory (1015) or accessories may be provided in adaptor kit (1020), maybe be provided separately, or may both be provided in the adaptor kit (1020) and provided separately, as may be the case for an accessory (1015) or any disposable accessories, for example.

The method (100) may further comprise a Memory-Storage Step (1910) of including a memory storage component (635) in each adaptor-kit cartridge (330) in the at least two adaptor kits or in any initial-state cartridge. The memory storage component (635) is computer memory configured to store a unique identifier or functionality profile. If each adaptor-kit cartridge (330) includes the memory storage component (635), then the method (100) may then further include a step of configuring the medical apparatus (335) to enable functionality based on the unique identifier and functionality profile. An example of a unique identifier may be a lengthy serial number, such as a 12-digit number to uniquely identify a specific adaptor-kit cartridge or to uniquely identify a specific functionality profile. An example of a functionality profile is a designation of a specific medical function enabled by the adaptor-kit cartridge (330) and the accessory (1015).

An Adaptor-kit cartridge (330) is an adaptor that physically or electronically interfaces with the medical apparatus (335) to add or enhance a medical function. The adaptor-kit cartridge (330) contains the necessary components, circuitry, sensors, or other elements required to enable the desired medical functionality when used with an accessory (1015).

The Initial-State Using Step (1408) is using the medical apparatus (335) to perform the initial-state function. This function may be chosen by the user or configured to run automatically by the medical apparatus (335).

The First-Altering Step (1415) is altering the medical apparatus (335) to perform a first new medical function by connecting to the medical apparatus (335) the adaptor-kit cartridge (330) for this first new medical function and by using the accessory (1015) in the adaptor-kit cartridge (330) for this first new medical function.

The First-Removing Step (1420) is removing the adaptor-kit cartridge (330) for the first new medical function and stopping use of the accessory (1015) for the first new medical function.

The Second-Altering Step (1425) is altering the medical apparatus (335) to perform a second new medical function by connecting to the medical apparatus (335) the adaptor-kit cartridge (330) for this second new medical function and by using the accessory (1015) for this second new medical function.

The Second-Removing Step (1430) is removing the adaptor-kit cartridge (330) for this second new medical function and stopping use of the accessory (1015) for this second new medical function.

The Third-Altering Step (1435) is altering the medical apparatus (335) to perform a third new medical function by connecting to the medical apparatus (335) the adaptor-kit cartridge (330) for this third new medical function and by using the accessory (1015) for this third new medical function.

The Performance Step (1505) is choosing the initial-state function for the medical apparatus (335) from one or more in the group consisting of: providing a status (1144) check, such as a battery status (1145); performing at least one pre-programmed self-test of the medical apparatus (335), firmware availability notification, or performing a firmware upgrade (1147); taking an electrocardiogram of a person (420), the electrocardiogram is also referred to as an ECG (1148); measuring blood pressure (1105) within the person (420); measuring blood composition (1110) within the person (420); measuring body temperature (1115) of the person (420); measuring a heart rate (1120) of the person (420); measuring chest acceleration (1125) of the person undergoing cardiopulmonary resuscitation (CPR); real-time therapeutic guidance in delivery of the medical function, that is coaching (1130); and performing external defibrillation of the person (420) using an AED (1135).

The medical apparatus (335) may be limited to enable each new medical function that requires an adaptor-kit cartridge (330) and an accessory (1015) or accessories only upon connection of the adaptor-kit cartridge (330) and use of the accessory (1015) or accessories that correspond to that medical function. Absent that correspondence, the medical function is preferably disabled. Preferably, that medical function is disabled in the absence of either the adaptor-kit cartridge (330) or the accessory (1015) or accessories required to enable the new medical function enabled by the adaptor-kit cartridge (330).

The Updating Step (1510) may include multiple steps. The Updating Step (1510) may include updating medical device firmware or software. The Updating Step (1510) may include the update (1141) of the firmware or software of the medical apparatus (335) that may be validated using at least one pre-programmed self-test of the medical apparatus (335), which may, for example, include an automated checksum or cyclic redundancy check (CRC) of the new software or firmware, an automated test of a medical apparatus (335) function after installation of the new software or firmware, or any other test that validates the update.

The Updating Step (1510) may include a step of providing status (1144) information about the medical apparatus (335), which may be received on the medical apparatus (335), via a connected device, or asynchronously through email or other interaction with a computer network. The update (1141) of the firmware or software is also referred to herein as an "updating sequence." Such update of software or firmware may involve the medical apparatus (335) automatically communicating with remote servers to detect available firmware of software, downloading available firmware or software, a user initiating a firmware or software update, and validation of installed firmware of software using at least one pre-programmed self-test to check the integrity of upgraded software or firmware on the medical apparatus (335). Downloading of software or firmware to the medical apparatus (335) may occur through a Wi-Fi connection between the medical apparatus (335) and network servers, may occur by a Bluetooth connection to a different device such as a smartphone, or may be occur using a wired connection to the medical apparatus (335). Steps that comprise the Updating Step (1510) may be performed in any sequence and need not be performed during a single user session. For example, as part of the Updating Step (1510), a user may receive a status, either on the medical apparatus (335) or on a connected smartphone, about the battery state of the medical apparatus (335) on a certain day; receive a status about an expired accessory (1015), either on the medical apparatus (335) or via an automated email a week later; receive an alert about an available firmware update the next day; initiate a firmware update three days later; and the medical apparatus (335) may perform certain automated self-tests every day.

In certain embodiments, processing and installation of software and firmware to the medical apparatus (335) may require a plurality of processors (645), that is at least two computer processors, within the medical apparatus (335) to perform a software or firmware update to the medical apparatus (335) when those software or firmware updates include changes in firmware or software that relate to one or more medical functions. When an update (1141) includes changes to firmware or software impacting one or more medical functions, coordination between the two or more processors may be required to install and validate the update (1141) to the medical function using at least one pre-programmed self-test to check the integrity of upgraded software or firmware on the medical apparatus (335). Thus, the Processor Step (1935) includes steps of including a plurality of processors (645) in the medical apparatus (335);

and configuring the plurality of processors (645) to install and validate an update (1141) of a medical function, the plurality of processors (645) configured to install and check the integrity of upgraded software or firmware on the medical apparatus (335). The term "upgrade" is used broadly to encompass any installation, reinstallation, modification, replacement, or initial deployment of computer code-whether firmware or software-on the medical apparatus (335), regardless of whether the code is new, revised, or identical to a previous version. Wherever the term "install" or "installation" is used in reference to computer code on the medical apparatus (335), it is intended to be encompassed within this definition of "upgrade."

For purposes of this disclosure, any computer code executing on one or more processors (645) included in the medical apparatus (335) is referred to as firmware. This includes software code stored in non-volatile memory, real-time operating system code, bootloaders, update handlers, diagnostic and test routines, signal processing instructions, and any other program logic that supports or controls the operation of the medical apparatus (335) and executes on one or more of its processors (645). Wherever the term "software" is used in reference to code executing on the medical apparatus (335), it is intended to be encompassed within this definition of firmware.

The medical apparatus (335) may use a segmented architecture with two or more processors to isolate and manage medical functions while allowing communications and other general processing to be handled by one or more separate communications processors. Medical functions are executed on one or more dedicated medical processors, which are secured by design and lack direct access to external communication channels such as Wi-Fi or Bluetooth. The medical processor or medical processors also uses real-time operating systems because they must execute time-critical tasks, such as ECG analysis and defibrillation control, with deterministic response times and high reliability-ensuring predictable behavior even under emergency conditions.

The communications processor or communications processors, by contrast, have access to external networks via technologies such as Bluetooth and Wi-Fi, and use that access to check for and download software or firmware updates, either wirelessly or via a wired connection. Downloads may occur automatically or require user interaction. If a user selects to install an update, the communications processor or communications processors initiate the update process. If the update includes software or firmware that runs on the medical processor or medical processors, the communications processor or communications processors transfer the new software or firmware to the medical processor or medical processors and coordinate with the medical processor or medical processors to perform the update.

Following this coordination, the medical processor or medical processors validate that the software or firmware has been properly installed using at least one pre-programmed self-test to check the integrity of the new software or firmware for the medical function or medical functions. Examples of such self-tests include automated checksum or cyclic redundancy check (CRC) routines, which confirm that the new software or firmware has not been corrupted or altered during transfer and installation. As used herein, a "processor" or "computer processor" refers to any circuit or logic device capable of executing instructions, including but not limited to general-purpose CPUs, microcontrollers, embedded processors, soft processors, application-specific integrated circuits (ASICs), digital signal processors (DSPs), and secure enclaves. The term encompasses processors with one or more cores, as well as processors that operate without a core-based architecture. A processor may include or be associated with volatile and/or non-volatile memory sufficient to store firmware, software, runtime data, and test logic necessary to execute the described functions.

The ECG Selecting Step (1515) includes multiple steps. A step is selecting the initial-state function as taking an electrocardiogram of the person (420). The electrocardiogram is also referred to herein as the ECG (835). The ECG Selecting Step (1515) further includes steps of: identifying a need for an ECG (835) from the person (420), the person (420) having bare skin (820) accessible to at least two separated sensors (340), the at least two separated sensors (340) operationally connected to the medical apparatus (335); and touching the bare skin (820) to the at least two separated sensors (340).

The Configuring Step (125) is configuring the at least two separated sensors to be functional when the person places a finger on each of the at least two separated sensors.

The Multiple Leads Step (1525) is providing the medical apparatus (335) with multiple leads (345) configured for taking the ECG.

The AED-Adaptor Step (205) is providing an AED adaptor kit (610). The AED adaptor kit (610) is configured to enable the medical apparatus (335) to perform a new medical function of a reusable non-wearable external defibrillator (AED), the AED adaptor kit (610) includes: an AED cartridge (630) and disposable-electrode pads (300).

The AED-Connecting Step (215) may also include steps of connecting the AED cartridge (630) to the medical apparatus (335) to enable its operation; and placing on the person (420) two of the disposable-electrode pads (300); and electrically connecting the disposable-electrode pads (300) to the medical apparatus (335) either directly or through the AED cartridge (630).

A unique relationship exists between the accessory (1015) and the adaptor-kit cartridge (330). The accessory (1015) may not independently be compatible with the medical apparatus (335). Compatibility is assured when used in conjunction with its corresponding adaptor-kit cartridge. When used together, the accessory (1015) and that adaptor-kit cartridge enables a medical function that could not otherwise be performed. For example, the AED-Adaptor Step (205) and the AED-Connecting Step (215) utilize disposable-electrode pads (300) connected via two wires to the AED cartridge (630), which then interfaces with the medical apparatus (335). This configuration supports a single-lead (ECG (835)), where electrical signals are received using a two-channel analog front end (AFE), a specific type of signal-acquisition and processing component.

As used herein, a "signal-acquisition and processing component" (845) refers to any hardware element or combination of elements configured to receive physiological signals of physiological parameters. The signal-acquisition and processing component (845) may be provided in the medical apparatus (335), may be provided in the adaptor-kit cartridge (330), or may be provided in both the medical apparatus (335) and the adaptor-kit cartridge (330). The signal-acquisition and processing component enables the medical apparatus (335) or the adaptor-kit cartridge (330) to condition or amplify physiological signals as needed, and perform at least analog-to-digital conversion or other processing necessary to prepare the physiologic signals for digital analysis by the medical apparatus. Examples include, but are not limited to, analog front ends (AFEs) for low-voltage bioelectric signals (925) (e.g., ECG, electromyography (EMG)), photodetectors and filters for photoplethysmographic (PPG) signals (e.g., $SpO_2$), pressure transducers for hemodynamic monitoring, and thermal sensors for temperature measurement.

An AFE (1035), as used herein, refers to a hardware circuit configured specifically to receive, amplify, and filter the low-voltage bioelectric signals (925) prior to digitization. By contrast, other physiological signals—such as those used for peripheral oxygen saturation ($SpO_2$), blood pressure, or temperature—may require different signal-acquisition and processing components.

In a preferred embodiment, the AED-Adaptor Step (205) utilizes the native two-channel AFE included in the medical apparatus (335) to acquire ECG (835) signals and enable detection of shockable arrhythmias.

By contrast, the Multiple Leads Step (1525) requires a substantially different configuration. The ECG accessory comprises multiple leads (345). The multiple leads (345) preferably include ten wires to capture a 12-lead ECG, which necessitates a 10-channel AFE for simultaneous signal acquisition. A preferred configuration of the medical apparatus (335) includes a native two-channel AFE and a data port (850) for communication with external AFE modules. In this case, the ECG adaptor-kit cartridge (1205) includes the required 10-channel AFE, and uses that 10-channel AFE instead of the native two-channel AFE, to process the raw analog signals from the accessory (1015), namely the multiple leads (345), connected to the bare skin (820) a person (420), and transmits digital ECG data to the medical apparatus (335) via the data port (850) for analysis, storage, or transmission. In some embodiments, the adaptor-kit cartridge (330) connects to the medical apparatus (335) data port (850) through the data connector (855) on the adaptor-kit cartridge (330).

In other embodiments, adaptor-kit cartridges configured for physiological monitoring may include one or more signal-acquisition and processing components, such as sensors and circuitry for acquiring and processing non-bioelectric signals, including photoplethysmographic data for $SpO_2$ estimation, mechanical data for non-invasive blood pressure measurement, or thermal data for temperature sensing. Thus, the adaptor-kit cartridge (330) is not merely a physical interface but performs essential signal acquisition and processing functions to support the medical function enabled by the accessory (1015).

This architecture enables the addition of previously unanticipated medical functions to the medical apparatus (335) through the use of purpose-configured adaptor-kit cartridges and associated accessories. By externalizing critical functional elements-such as sensing, signal processing, therapeutic delivery, or other operational logic-into the adaptor-kit cartridge (330), the system provides a modular, extensible platform in which the core of the medical apparatus (335) can support a wide variety of medical functions without hardware redesign. That is, additional medical functions are enabled through use of the adaptor-kit cartridge (330) and the accessory (1015), without altering the internal hardware or circuitry of the medical apparatus (335). These functions may range from patient monitoring and diagnostic evaluation to therapeutic interventions, including those not foreseen at the time of manufacture. This level of adaptability represents a substantial departure from conventional medical devices, which are typically limited to a fixed, pre-defined set of capabilities. The resulting architecture supports field-configurable expansion, faster adoption of emerging clinical techniques, and improved lifecycle utility of the base device.

In one embodiment, the medical apparatus (335) comprising a housing (920) configured to be hand-held (425), the medical apparatus (335) further comprising a processor (1030) and an analog front end (AFE), the AFE (1035) configured to receive low-voltage bioelectric signals (925); a plurality of adaptor-kit cartridges, each adaptor-kit cartridge (330), in the plurality of adaptor-kit cartridges, is configured to removably attach to and operationally integrate with the medical apparatus (335); a plurality of accessories, each accessory (1015), in the plurality of accessories, is configured for use with an adaptor-kit cartridge (330), each adaptor-kit cartridge (330) comprising circuitry (840) configured to enable a medical function when used with the accessory (1015); at least one adaptor-kit cartridge (330) comprises a signal-acquisition-and-processing component (845), not present in the medical apparatus (335), that is configured to perform at least analog-to-digital conversion of a physiological signal; the medical apparatus (335) configured to perform an initial-state function, and to perform a medical function upon attachment and integration of an adaptor-kit cartridge (330) and upon use of the accessory (1015); and the medical apparatus (335) includes a modular interface (650) configured to receive a plurality of adaptor-kit cartridges, wherein each adaptor-kit cartridge (330), in the plurality of adaptor-kit cartridges, enables a new medical function when used with the accessory (1015), without altering the internal hardware or circuitry of the medical apparatus (335).

In a preferred embodiment, each adaptor-kit cartridge (330) includes a memory storage component (635) configured to store a globally unique identifier. Upon connection to the medical apparatus (335), the identifier is read and used to confirm cartridge authenticity, determine compatibility, and enable the corresponding medical function. For example, a unique identifier may trigger the activation of functions for automated defibrillation, wearable AED operation, ECG recording, or internal defibrillation based on the adaptor kit (1020). This embodiment ensures that only verified and intended cartridges enable functionality, providing both safety and modularity.

The medical apparatus (335) may be configured to perform the medical function without attaching and operationally integrating an adaptor-kit cartridge (330) and the medical apparatus (335) may be configured to perform the medical function without using an accessory (1015).

Figure 16:
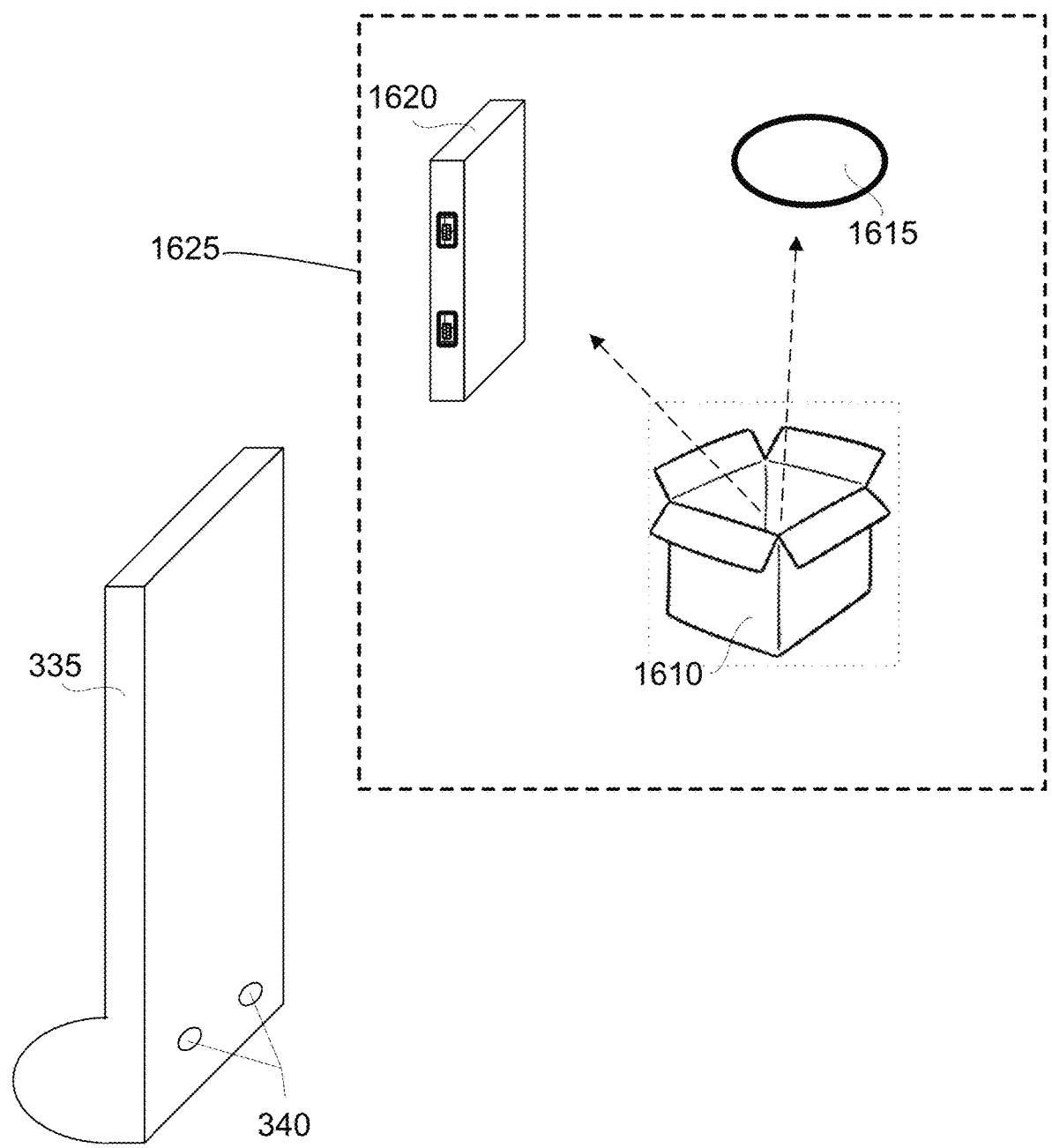
FIG. 16 illustrates the contents of a training adaptor kit and the medical apparatus.

The Training Step (1730) includes a step of providing a training adaptor kit (1610); and a step of altering the medical apparatus (335) to perform a new initial-state function by connecting a training adaptor-kit cartridge (1620) and by using a training accessory (1615). The contents of the training adaptor kit (1610) are illustrated in the dashed box (1625) in FIG. 16. Because training is not considered a medical function for purposes of this specification, the training adaptor-kit cartridge (1620) does not enable an initial-medical function. However, if the training adaptor-kit cartridge (1620) is connected at the time the medical apparatus (335) becomes active, the training adaptor-kit cartridge (1620) enables the initial-state function of AED training.

The training adaptor kit (1610) comprises a training adaptor-kit cartridge (1620) and a training accessory (1615). Preferably, the training accessory (1615) may include training-electrode pads, which are preferably reusable, non-conductive pads that simulate electrode placement and medical apparatus (335) interaction during a training exercise. Alternatively, the training-electrode pads may be disposable-electrode pads (300) and able to be replaced by adding multiple training-electrode pads to the training adaptor kit (1610) or packaging external to the training adaptor kit. The training-electrode pads serve as an example of an accessory (1015) that allows users to practice pad placement and AED operation in a non-therapeutic setting. Other training accessories (1615) may include additional components, such as simulation cables, visual indicators, or feedback systems that enhance the training experience.

Preferably, the training adaptor-kit cartridge (1620) is automatically recognized by the medical apparatus (335) upon connection, prompting the device to enter a dedicated training mode. This recognition may occur through embedded identifiers, electronic signaling, or other detection mechanisms that differentiate the training cartridge from therapeutic cartridges. Preferably, upon activation, the medical apparatus (335) adjusts its interface to disable shock functionality and modify user prompts and display behavior accordingly. Preferably, no electrical connection is made to the training electrode pads. This automatic transition ensures seamless operation and intuitive user interaction while reinforcing best practices in AED deployment and patient care.

The medical apparatus (335) may also have features to disable radio transmissions. Radio transmissions include BLUETOOTH tooth or wireless transmission. Transmissions may be disabled using the Transmission-Disabling Step (1925) which is a step of disabling radio transmissions from the medical apparatus (335) by activating a switch (640) for the medical apparatus (335). The switch (640) may be an external button selectable by a user or may be an electronic control selectable by the user.

The Function Step (1930) includes steps of: setting two initial-state functions comprising the updating sequence and a pre-programmed self-test, the updating sequence comprising automatically detecting an availability of a firmware or software update; receiving user initiation to update the firmware or software; and validating the software or firmware update using the pre-programmed self-test.

The wAED-Adaptor Step (221) is providing a wAED adaptor kit (710), the wAED adaptor kit (710) configured to enable the medical apparatus (335) to perform a new medical function of a wearable automated external defibrillator (wAED), the wAED adaptor kit (710) comprises a wAED cartridge (730) configured to connect with, and operationally integrate with, the medical apparatus (335).

The Storing-wAED-Pads Step (1320) further requires the wAED adaptor kit (710) to be configured to store disposable-electrode pads (300). Preferably, there are at least two disposable-electrode pads.

The wAED-Harness Step (222) is providing a harness in the wAED adaptor kit; and securing the harness on a person (420).

The wAED-Connecting Step (1325) is connecting the wAED cartridge (730) to the medical apparatus (335); and attaching the disposable-electrode pads (300) to the person (420).

The ECG-Providing Step (1330) is providing an ECG adaptor kit (1200), the ECG adaptor kit (1200) is configured to enable the medical apparatus (335) to perform a third new medical function of taking an electrocardiogram (ECG (835)), the ECG adaptor kit (1200) comprising: an ECG adaptor-kit cartridge (1205); and a plurality of sensors (1210) configured to measure a magnitude and direction of electrical currents in a heart during each heartbeat. The plurality of sensors (1210) is shown within the dashed box in FIG. 12.

The Initial-state function may be one of three types: an initial-medical function, an operational readiness check that may be required to ensure that medical apparatus (335) is ready and able to execute one or more medical functions, or a function that supports medical functions after those operational readiness functions are complete (e.g., uploading ECG data to the cloud upon completion of the ECG (835)).

Thus, an initial-state function is a medical function or supports one or more medical functions. An initial-state function becomes active, whether due to user interaction (such as pressing a button or upon the device waking from a lower-power mode) or an automatic event. An initial state function may, as non-limiting examples, include providing a status (1144) check, providing a pad status (1149) on the disposable-electrode pads (300), providing an ECG pads status (1146) performing a self-test (1143) of the medical apparatus (335), which may be pre-programmed, firmware (1147) availability notification, or firmware (1147) upgrade.

INDUSTRIAL APPLICABILITY

The invention has application to the emergency medical industry.

What is claimed is:

1. A method of using a medical apparatus, the method comprising the steps of:
providing a medical apparatus configured to be hand-held and further configured in an initial state to perform a medical treatment of a living body;
connecting to the medical apparatus a first adaptor-kit cartridge and using a first accessory configured to enable the medical apparatus to perform a first new medical function selected from the group consisting of a diagnostic function, a monitoring function, and a medical treatment of a living body, the first adaptor-kit cartridge and the first accessory are further configured to be used together when the first adaptor-kit cartridge is operationally integrated into the medical apparatus;
connecting to the medical apparatus a second adaptor-kit cartridge and using a second accessory configured to enable the medical apparatus to perform a second new medical function selected from the group consisting of a diagnostic function, a monitoring function, and a medical treatment of a living body, the second adaptor-kit cartridge and the second accessory are further configured to be used together when the second adaptor-kit cartridge is operationally integrated into the medical apparatus;
providing the first adaptor-kit cartridge, the second adaptor-kit cartridge, the first accessory and the second accessory;
using the medical apparatus to perform the medical treatment;
transforming the medical apparatus to perform the first new medical function by connecting to the medical apparatus the first adaptor-kit cartridge and by using the first accessory;
removing the first adaptor-kit cartridge and stopping use of the first accessory; and
transforming the medical apparatus to perform the second new medical function by connecting to the medical apparatus the second adaptor-kit cartridge and by using the second accessory.

2. The method of claim 1, further comprising the steps of:
removing the second adaptor-kit cartridge for the second new medical function and stopping use of the second accessory; and altering the medical apparatus to perform a third new medical function by connecting to the medical apparatus a third adaptor-kit cartridge and by using a third accessory.

3. The method of claim 1, further comprising the steps of: choosing an initial-state function for the medical apparatus from the group consisting of:
providing a status check;
performing at least one pre-programmed self-test of the medical apparatus;
providing a firmware availability notification;
performing a firmware upgrade;
taking an electrocardiogram (ECG) of a person;
measuring blood pressure within the person;
measuring blood composition within the person;
measuring body temperature of the person;
measuring a heart rate of the person;
measuring acceleration of a chest of the person undergoing cardiopulmonary resuscitation (CPR);
real-time therapeutic guidance in delivery of a medical function; and
performing automated external defibrillation of the person.

4. The method of claim 1, further comprising the steps of:
updating medical device firmware;
performing at least one pre-programmed self-test of the medical apparatus; and
providing status information about the medical apparatus.

5. The method of claim 1, further comprising the steps of:
selecting an initial-state function for the medical apparatus as taking an electrocardiogram (ECG) of a person; identifying a need for an electrocardiogram from a person, the person having bare skin accessible to at least two separated sensors, the at least two separated sensors operationally connected to the medical apparatus; and
touching the bare skin to the at least two separated sensors.

6. The method of claim 5, further comprising the step of configuring the at least two separated sensors to be functional when the person places a finger on each of the at least two separated sensors.

7. The method of claim 5, further comprising the step of providing the medical apparatus with multiple leads configured for taking the ECG.

8. The method of claim 1, further comprising the step of: providing an AED adaptor kit, the AED adaptor kit configured to enable the medical apparatus to perform a new medical function of a reusable non-wearable external defibrillator (AED), the AED adaptor kit comprises: an AED cartridge and disposable-electrode pads.

9. The method of claim 8, further comprising the steps of:
connecting the AED cartridge to the medical apparatus to enable its operation; and
placing on a person two disposable-electrode pads.

10. The method of claim 8, further comprising the step of configuring the AED cartridge to store each of the disposable-electrode pads while each such disposable electrode pad is electrically connected to the AED cartridge.

11. The method of claim 8, further comprising the step of enabling the medical apparatus to perform a new medical function of a reusable non-wearable automated external defibrillator.

12. The method of claim 1, further comprising the steps of:
providing an internal defibrillation kit, the internal defibrillation kit comprising an internal-defibrillation cartridge and internal-defibrillation paddles configured for internal defibrillation;
connecting the internal-defibrillation cartridge to the medical apparatus to enable manual defibrillation;
connecting the internal-defibrillation paddles to the medical apparatus through the internal-defibrillation cartridge; and
placing the internal-defibrillation paddles directly onto a person's heart for defibrillation.

13. The method of claim 1, further comprising the steps of:
providing an internal defibrillation kit, the internal defibrillation kit comprising an internal-defibrillation cartridge and internal-defibrillation paddles that are pre-connected to the internal-defibrillation cartridge, the internal-defibrillation paddles configured for internal defibrillation;
connecting the internal-defibrillation cartridge to the medical apparatus; and
placing the internal-defibrillation paddles directly onto a person's heart for defibrillation.

14. The method of claim 1, further comprising the steps of:
providing a wearable automated external defibrillator (wAED) adaptor kit, the wAED adaptor kit configured to enable the medical apparatus to perform a new medical function of a wAED, the wAED adaptor kit comprising a wAED cartridge configured to connect to, and operationally integrate with, the medical apparatus; an accessory is also provided.

15. The method of claim 14, further comprising the steps of: providing a harness as the accessory; and securing the harness on a person.

16. The method of claim 14, further comprising the steps of: providing disposable wAED electrode pads; and further configuring the wAED adaptor kit to store the disposable wAED electrode pads.

17. The method of claim 14, further comprising the steps of:
connecting the wAED cartridge to the medical apparatus; and
attaching two disposable-electrode pads to a person.

18. The method of claim 1, further comprising the step of:
providing an ECG adaptor kit, the ECG adaptor kit configured to enable the medical apparatus to perform a medical function of taking an electrocardiogram (ECG), the ECG adaptor kit comprising: an ECG cartridge; and a plurality of sensors configured to measure a magnitude and direction of electrical currents in a heart during each heartbeat.

19. The method of claim 1, further comprising the step of:
providing a training adaptor kit, the training adaptor kit configured to enable the medical apparatus to perform a new initial-state function of training a person to use the medical apparatus as an AED.

20. The method of claim 1, further comprising the step of configuring the medical apparatus to be hand-held so as to be held in a single adult hand while being used.

21. The method of claim 1, further comprising the steps of: including a memory storage component in the first adaptor-kit cartridge and the second adaptor-kit cartridge, the memory storage component configured to store a unique identifier; and further configuring the medical apparatus to enable functionality based on the unique identifier.

22. The method of claim 1, further comprising the step of: setting an initial-state function of the medical apparatus by connecting to the medical apparatus at least one adaptor-kit cartridge prior to activating the medical apparatus, the at least one adaptor-kit cartridge configured for use with at least one accessory.

23. The method of claim 1, further comprising the step of: disabling radio transmissions from the medical apparatus by activating a switch for the medical apparatus.

24. The method of claim 1, further comprising the step of separately framing the first adaptor-kit cartridge and the second adaptor-kit cartridge in a housing configured to connect with the medical apparatus, and wherein the first adaptor-kit cartridge enables a medical function selected from the group consisting of: cardiac defibrillation, cardiac pacing, and electrocardiography.

25. The method of claim 1, further comprising the steps of: including a plurality of processors in the medical apparatus; and configuring the plurality of processors to install and validate a firmware upgrade for a medical function, the plurality of processors configured to install and check for integrity of the firmware for a medical function on the medical apparatus.

26. The method of claim 1, further comprising the steps of:
setting two initial-state functions comprising an updating sequence and a pre-programmed self-test, the updating sequence comprising automatically detecting an availability of a firmware update;
receiving user initiation to update the firmware; and
validating the firmware update using the pre-programmed self-test.

27. A method of using a medical apparatus, the method comprising the steps of:
providing a medical apparatus configured to be hand-held and further configured in an initial state to perform a medical treatment of a living body;
the medical apparatus further configured to be transformed to perform a new medical function by connecting to the medical apparatus a first adaptor-kit cartridge and using a first accessory, the first adaptor-kit cartridge and the first accessory configured to be used together and further configured to operationally integrate with the medical apparatus;
the medical apparatus further configured to be transformed to perform a second new medical function by connecting to the medical apparatus a second adaptor-kit cartridge and using a second accessory, the second adaptor-kit cartridge and the second accessory configured to be used together and further configured to operationally integrate with the medical apparatus;
the medical apparatus further configured to be transformed to perform a third new medical function by connecting to the medical apparatus a third adaptor-kit cartridge and using a third accessory, the third adaptor-kit cartridge and the third accessory configured to be used together and further configured to operationally integrate with the medical apparatus;
providing the first adaptor-kit cartridge, the second adaptor-kit cartridge, the third adaptor-kit cartridge, the first accessory, the second accessory and the third accessory;
using the medical apparatus to perform the medical treatment;
installing the first adaptor-kit cartridge, the second adaptor-kit cartridge, and the third adaptor-kit cartridge individually and each in a separate housing each separately configured to connect with the medical apparatus, and wherein the first adaptor-kit cartridge together with the first accessory, the second adaptor-kit cartridge together with the second accessory, and the third adaptor-kit cartridge together with the third accessory each separately enable a new medical function selected from the group consisting of: cardiac defibrillation, cardiac pacing, and electrocardiography;
transforming the medical apparatus to perform a first new medical function by connecting to the medical apparatus the first adaptor-kit cartridge and by using the first accessory;
removing the first adaptor-kit cartridge and stopping use of the first accessory;
transforming the medical apparatus to perform a second new medical function by connecting to the medical apparatus the second adaptor-kit cartridge and by using the second accessory;
removing the second adaptor-kit cartridge and stopping use of the second accessory; and
transforming the medical apparatus to perform a third new medical function by connecting to the medical apparatus the third adaptor-kit cartridge and by using the third accessory.

28. A medical apparatus comprising:
a housing configured to be hand-held, the medical apparatus further comprising a processor and an analog front end (AFE), the AFE configured to receive bioelectric signals;
a plurality of adaptor-kit cartridges, each adaptor-kit cartridge, in the plurality of adaptor-kit cartridges, is configured to removably attach to and operationally integrate with the medical apparatus;
a plurality of accessories, each accessory, in the plurality of accessories, is configured for use with an adaptor-kit cartridge in the plurality of adaptor-kit cartridges, each adaptor-kit cartridge in the plurality of adaptor-kit cartridges comprising circuitry configured to enable a new medical function when used with the accessory;
at least one adaptor-kit cartridge comprises a signal-acquisition-and-processing component, the signal-acquisition-and-processing component configured to perform at least analog-to-digital conversion of a physiological signal;
the medical apparatus configured to perform a medical treatment of a living body; and
a modular interface configured to receive a plurality of adaptor-kit cartridges, wherein each adaptor-kit cartridge, in the plurality of adaptor-kit cartridges, enables a new medical function when used with an accessory, without altering the internal hardware or circuitry of the medical apparatus.

29. The medical apparatus of claim 28, wherein the medical apparatus is configured to perform the medical treatment of a living body without attaching and operationally integrating an adaptor-kit cartridge and using an accessory.

30. The medical apparatus of claim 28, wherein the medical apparatus is not configured to perform the medical treatment of a living body without attaching and operationally integrating an adaptor-kit cartridge and using an accessory.

* * * * *